US011826344B2

(12) United States Patent
Adesina

(10) Patent No.: US 11,826,344 B2
(45) Date of Patent: Nov. 28, 2023

(54) COMPOSITION, METHOD OF MANUFACTURE, AND USE OF SITE-SPECIFIC DELIVERY OF BRUCEOLIDES FOR TREATMENT OF CANCER AND OTHER DISEASES

(71) Applicant: HOWARD UNIVERSITY, Washington, DC (US)

(72) Inventor: Simeon Kolawole Adesina, Mitchellville, MD (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 15/775,986

(22) PCT Filed: Nov. 18, 2016

(86) PCT No.: PCT/US2016/062833
§ 371 (c)(1),
(2) Date: May 14, 2018

(87) PCT Pub. No.: WO2017/087835
PCT Pub. Date: May 26, 2017

(65) Prior Publication Data
US 2018/0325865 A1 Nov. 15, 2018

Related U.S. Application Data

(60) Provisional application No. 62/350,439, filed on Jun. 15, 2016, provisional application No. 62/257,633, filed on Nov. 19, 2015.

(51) Int. Cl.
| | | |
|---|---|---|
| *A61K 31/366* | (2006.01) | |
| *A61K 31/337* | (2006.01) | |
| *C07D 493/20* | (2006.01) | |
| *A61K 47/64* | (2017.01) | |
| *A61P 35/00* | (2006.01) | |
| *A61K 38/00* | (2006.01) | |
| *A61K 9/51* | (2006.01) | |

(52) U.S. Cl.
CPC .......... *A61K 31/366* (2013.01); *A61K 9/5146* (2013.01); *A61K 9/5184* (2013.01); *A61K 31/337* (2013.01); *A61K 47/64* (2017.08); *A61P 35/00* (2018.01); *C07D 493/20* (2013.01); *A61K 38/00* (2013.01)

(58) Field of Classification Search
CPC .... A61K 31/337; A61K 31/366; A61K 38/00; A61K 47/64; A61K 9/5146; A61K 9/5184; A61P 35/00; C07D 493/20
See application file for complete search history.

(56) References Cited

U.S. PATENT DOCUMENTS

| | | | | |
|---|---|---|---|---|
| 6,573,296 | B2 * | 6/2003 | Grieco | A61K 31/366 |
| | | | | 514/453 |
| 8,361,932 | B2 * | 1/2013 | Liu | G01N 33/57434 |
| | | | | 506/18 |
| 8,921,429 | B2 * | 12/2014 | Akala | A61K 31/337 |
| | | | | 514/772.3 |
| 9,675,556 | B2 * | 6/2017 | Akala | A61K 31/337 |
| 2002/0019439 | A1 | 12/2002 | Grieco et al. | |
| 2002/0193425 | A1 * | 12/2002 | Pezzuto | A61K 31/366 |
| | | | | 514/453 |
| 2006/0281807 | A1 * | 12/2006 | McChesney | C07D 493/08 |
| | | | | 514/453 |
| 2012/0237533 | A1 * | 9/2012 | Kulik | C07K 16/3069 |
| | | | | 424/94.5 |
| 2012/0309819 | A1 | 12/2012 | McChesney et al. | |

FOREIGN PATENT DOCUMENTS

WO  WO-9852966 A1 * 11/1998 ............. A61K 31/33

OTHER PUBLICATIONS

Hall et al., "Antitumor Agents XLII: Comparison of Antileukemic Activity of Helenalin, Brusatol, and Bruceantin and Their Esters on Different Strains of P-388 Lymphocytic Leukemic Cells", 1981, Journal of Pharmaceutical Sciences, 70(10), pp. 1147-1150. (Year: 1981).*
Tang et al., "Novel Nitric Oxide-Releasing Derivatives of Brusatol as Anti-Inflammatory Agents: Design, Synthesis, Biological Evaluation, and Nitric Oxide Release Studies", 2014, J. Med. Chem., 57(18), pp. 7600-7612. (Published: Sep. 2, 2014) (Year : 2014).*
Estanqueiro et al., "Nanotechnological carriers for cancer chemotherapy: The state of the art", 2015, Colloids and Surfaces B: Biointerfaces, vol. 216, pp. 631-648. (Available online Jan. 3, 2015) (Year: 2015).*
Mishra et al., "PEGylation in anti-cancer therapy: An overview", 2016, Asian Journal of Pharmaceutical Sciences, 2016, 11(3), pp. 337-348. (Available online Sep. 14, 2015) (Year: 2016).*
Zhang et al., "Redox-sensitive micelles composed of disulfidelinked Pluronic-linoleic acid for enhanced anticancer efficiency of brusatol", 2018, International Journal of Nanomedicine, vol. 13, pp. 939-956. (Year: 2018).*
Nienaber et al., "A glutamic acid specific serine protease utilizes a novel histidine triad in substrate binding", 1993, Biochemistry, 32 (43), pp. 11469-11475. (doi.org/10.1021/bi00094a001) (Year: 1993).*
López-Otín et al., "Proteases: Multifunctional Enzymes in Life and Disease", 2008, J. Biol. Chem., 283(45), pp. 30433-30437. (doi: 10.1074/jbc.R800035200) (Year: 2008).*

(Continued)

Primary Examiner — My-Chau T. Tran
(74) Attorney, Agent, or Firm — Sughrue Mion, PLLC

(57) ABSTRACT

Disclosed are bruceolides for the treatment of cancer, and other diseases, selectively targeting unwanted cells. The disclosed bruceolides may include a site specific cleavable moiety inhibiting the chemotoxic activity until cleaved, i.e., removed, within and/or near a cancer to be treated. As to facilitate selective delivery to cancer tumors, the disclosed bruceolides may be loaded into, attached to or otherwise carried by nanoparticles.

15 Claims, 14 Drawing Sheets
Specification includes a Sequence Listing.

(56) References Cited

OTHER PUBLICATIONS

Ménez et al., "Crystal Structure of a Ternary Complex between Human Prostate-specific Antigen, Its Substrate Acyl Intermediate and an Activating Antibody", 2008, J. Mol. Biol., 376(4), pp. 1021-1033. (https://doi.org/10.1016/j.jmb.2007.11.052) (Year: 2008).*

Lawrence et al., "Kallikreins on Steroids: Structure, Function, and Hormonal Regulation of Prostate-Specific Antigen and the Extended Kallikrein Locus", 2010, Endocrine Reviews, vol. 31, Issue 4, pp. 407-446. (https://doi.org/10.1210/er.2009-0034) (Year: 2010).*

Denmeade et al., "Specific and Efficient Peptide Substrates for Assaying the Proteolytic Activity of Prostate-specific Antigen", 1997, Cancer Res., 57(21), pp. 4924-4930. (Year: 1997).*

Lizbeth Hedstrom, "Serine Protease Mechanism and Specificity", 2002, Chem. Rev., 102(12), pp. 4501-4523. (Year: 2002).*

Rahman et al., "Three New Quassinoid Derivatives and Related Compounds as Antitumor Promoters from Brucea javanica", 1999, Bulletin of the Chemical Society of Japan, 72(4), pp. 751-756. (https://doi.org/10.1246/bcsj.72.751) (Year: 1999).*

Chen et al., "Chemical components, pharmacological properties, and nanoparticulate delivery systems of Brucea javanica", 2013, International Journal of Nanomedicine, 8(1), pp. 85-92. (https://doi.org/10.2147/IJN.S31636) (Year: 2013).*

Patent Cooperation Treaty, International Search Report and Written Opinion of the International Searching Authority dated Jan. 27, 2017 for International Application No. PCT/US2016/062833, 9 pages.

Akinboye, Emmanuel S., et al., "Design, Synthesis, and Evaluation of pH-Dependent Hydrolyzable Emetine Analogues as Treatment for Prostate Cancer," Journal of Medicinal Chemistry, vol. 55, 2012, pp. 7450-7459.

Akinboye, Emmanuel S., et al., "Anticancer activities of emetine prodrugs that are proteolytically activiated by the prostate specific antigen (PSA) and evaluation of in vivo toxicity of emetine derivatives," Bioorganic & Medicinal Chemistry, vol. 25, 2017, pp. 6707-6717.

Jain, Nareshkumar, et al., "Current ADC Linker Chemistry," Pharmaceutical Research, vol. 32, 2015, pp. 3526-3540.

Jiang, Lan, et al., "A pH-sensitive nano drug delivery system of doxorubicin-conjugated amphiphilic polyrotaxane-based block copolymers," Biomaterials Science, vol. 1, 2013, pp. 1282-1291.

Kumar, Srinivas K., et al., "Modulating paclitaxel bioavailability for targeting prostate cancer," Bioorganic & Medicinal Chemistry, vol. 15, 2007, pp. 4973-4984.

* cited by examiner

COMPOSITION, METHOD OF MANUFACTURE, AND USE OF SITE-SPECIFIC DELIVERY OF BRUCEOLIDES FOR TREATMENT OF CANCER AND OTHER DISEASES

CROSS-REFERENCE TO RELATED APPLICATIONS

This application is a U.S. national phase application filed under 35 U.S.C. § 371 of International Application Number PCT/US2016/062833, filed Nov. 18, 2016, designating the United States, which claims benefit of U.S. Provisional Application No. 62/350,439, filed Jun. 15, 2016, and U.S. Provisional Application No. 62/257,633, filed Nov. 19, 2015.

INCORPORATION BY REFERENCE OF SEQUENCE LISTING

In compliance with the 37 C.F.R. § 1.52(e)(5), the content of the ASCII text file named "Replacement_sequence_listing", which is 506 bytes in size and created on Jun. 22, 2023, is hereby incorporated by reference in its entirety.

FIELD

The present application generally relates to bruceolides, which include analogs and prodrugs thereof, for the treatment of disease and delivery systems encapsulating and/or carrying bruceolides.

BACKGROUND

Cancers are often treated with chemotherapeutic agents that are toxic to cancer cells. Brusatol, isolated from evergreen shrub *Brucea javanica* (L) has been reported to inhibit Nrf2 signaling. By this mechanism, it has been reported to reduce tumor burden and ameliorate chemoresistance in both in vitro and in vivo cancer models. In addition to this, previous data using rabbit reticulocytes has shown that brusatol inhibits eukaryotic protein synthesis. Accordingly, brusatol is a known chemotherapeutic agent shown effective in some cancer cell lines.

Unfortunately, as cancers are uncontrolled growths of normal cells, chemotherapeutic agents that kill cancer cells are also toxic to healthy cells. Consequently, chemotherapeutic agents are toxic to both the patient and the cancer to be treated. The battle then for treating cancer becomes a struggle to kill the unwanted cancer cells without further harming the patient, by preferentially or selectively killing cancer cells over noncancerous cells.

Past efforts have focused on limiting the amount of chemotherapy as to allow the patient to recover between treatment sessions. This, however, also gives the cancer time to recover. As the cancer recovers, it may develop a resistance to the chemotherapeutic agents, giving rise to incidences of drug resistance referred to as chemoresistance. As to limit the ability of the cancer to recover, efforts have been made to titrate the dose of chemotherapeutic agents administered during chemotherapy so that the cancer cells are killed at a faster rate than healthy cells. Both approaches leave the patient weak, suffering from both the disease and the treatment.

SUMMARY

Disclosed are bruceolides, which include analogs and derivatives thereof, for the treatment of cancer, arthritis, malaria and other diseases, that selectively target diseased cells. For example, such compounds may include, but are not limited to, brusatol, esters of brusatol, bisbrusatol esters, bruceatin, bruceines A, B, C, D, E, F, G, glycosidic bruceolides, aglycones, other quassinoids, and intermediates. Bruceolides are protein synthesis inhibitors that inhibit the ability of cells to produce the proteins needed to survive. As a result of this general method of action, bruceolides are potentially toxic to healthy cells. However, when selectively targeted to unwanted cells, such as cancer cells, bruceolides exert a primary cytotoxic effect. That is bruceolides kill cancer cells without the aid of additional chemotherapeutic agents. As to facilitate selective targeting to unwanted cells, such as prostate cancer, a bruceolide may comprise a site specific cleavable moiety inhibiting its chemotherapeutic activity, such that the bruceolide displays an inhibited chemotherapeutic effect until the selectively cleavable moiety is removed and an increased chemotherapeutic effect when all or a part of the selectively cleavable moiety is removed. Accordingly, in some embodiments the bruceolide may be a site specific prodrug of a chemotherapeutic agent.

Some embodiments of bruceolides prodrugs to chemotherapeutic agents may be represented by the following formula:

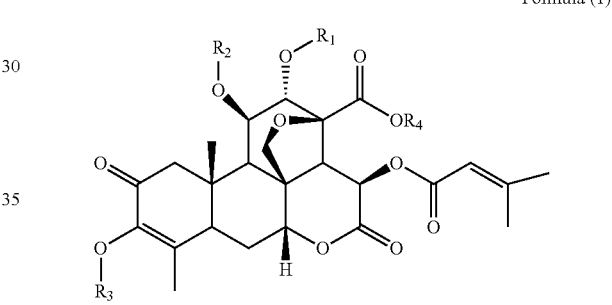

Formula (1)

wherein, $R_1$, $R_2$, $R_3$ and $R_4$ are selected from a site specific cleavable moiety, an alkyl, and a hydrogen. In one form, the chemotherapeutic agent may take the form of or otherwise be incorporated into a nanoparticle. The nanoparticle may help inhibit activity of the bruceolide until it is within or near the site to be treated.

In some embodiments at least one of $R_1$, $R_2$, $R_3$ and $R_4$ is a site specific cleavable moiety. The site specific cleavable moiety at $R_1$, $R_2$, $R_3$ and/or $R_4$ may inhibit the activity of the bruceolide until cleaved, i.e., removed, within and/or near the site of the disease to be treated. As to facilitate cleavage, site specific cleavable moieties may include at least one linker comprising a bond that is broken when a bruceolide according to Formula (1) is within and/or near the site of the disease to be treated. Accordingly, a bruceolide according to Formula (1) may be a prodrug of a cytotoxic agent having no or diminished cytotoxic effect until the site specific cleavable moiety is removed. Site specific cleavable moieties at least one of $R_1$, $R_2$, $R_3$ and $R_4$ may therefore provide site-specific activation of a non-toxic prodrug.

As to selectively transform a prodrug according to Formula (1) into its full cytotoxic form when within and/or near a tumor to be treated, the site specific cleavable moiety may be sensitive, i.e., cleavable, by an enzyme expressed by the disease be treated. As to lessen the impact of the cytotoxic agent on healthy cells, the enzyme to which the selectively cleavable moiety is sensitive may be selectively expressed in and/or near the site of the disease to be treated. In combination or the alternative, the enzyme to which the selectively cleavable moiety is sensitive may be over expressed in and/or near the site of the disease to be treated. For example, when a bruceolide according to Formula (1) is administered to treat prostate cancer, at least one of $R_1$, $R_2$, $R_3$ and $R_4$ may be a site specific cleavable moiety may be sensitive to prostate specific antigen. Sensitivity to prostate specific antigen may be imparted by including within the moiety a bond that is broken by prostate specific antigen. In combination or the alternative, sensitivity to prostate specific antigen may be imparted by including within the site specific cleavable moiety a linker comprising a bond that is broken by prostate specific antigen.

In one form, the site specific cleavable moiety may be a sensitive to environmental conditions present within and/or near the site of the disease to be treated. That is the site specific cleavable moiety may be removed when a bruceolide according to Formula (1) is exposed to environmental conditions present within and/or near the site of the disease to be treated. In some embodiments, for example, the site specific cleavable moiety may be sensitive to such that all or a portion of the moiety is removed when exposed to a certain pH.

In addition to or in the alternative to being sensitive to prostate specific antigen, at least one of $R_1$, $R_2$, $R_3$ and $R_4$ may be a site specific cleavable moiety sensitive to glutathione. Sensitivity to glutathione may be imparted by including in at least one of $R_1$, $R_2$, $R_3$ and $R_4$ a disulfide bond. In combination or the alternative, sensitivity to glutathione may be imparted by including in at least of $R_1$, $R_2$, $R_3$ and $R_4$ a linker comprising a disulfide bond. Accordingly, in variants of Formula (1) at least one of $R_1$, $R_2$, $R_3$ and $R_4$ may comprise a peptide moiety containing a cystine. Sensitivity to glutathione may also be imparted by including in at least one of $R_1$, $R_2$, $R_3$ and $R_4$ may comprise a linker molecule comprising a disulfide bond. For instance, at least one of $R_1$, $R_2$, $R_3$ and $R_4$ may comprise a linker including cystine.

Site specific cleavable moieties at $R_1$, $R_2$, $R_3$ and $R_4$ are not limited to peptide moieties containing at least one amino acid residue, but rather may include any combination of other components to conjugate the drug to the particle. Such materials include, but are not limited to, peptide moieties, carbohydrate moieties, and glycoprotein moieties.

As to facilitate selective delivery to the site of the disease to be treated, at least one of $R_1$, $R_2$, $R_3$ and $R_4$ in Formula (1) may be a site specific cleavable moiety connected to a nanoparticle. For instance, cancer tumors displaying enhanced permeability and retention effect contain gaps between the cells into which nanoparticles may settle. As such gaps are less prevalent in healthy tissue, nanoparticles may selectively settle within tumors thereby facilitating selective drug delivery. In combination or the alternative, bruceolides according to Formula (1) may be loaded, attached, and/or formed into the nanoparticles.

Nanoparticles having attached or encapsulated bruceolides according Formula (1), having bruceolides according to Formula (1) loaded therein and/or otherwise carrying bruceolides according to Formula (1) may be as small as 20 nm in diameter. Nanoparticles carrying bruceolides may be between 250 nm and 315 nm in diameter. Nanoparticles as large as 800 nm in diameter may also be used to carry bruceolides according to Formula (1).

When bruceolides according to Formula (1) are loaded into nanoparticles, the loading may be between 0.1% and 50%. Effective embodiments may also include loadings between 0.2% and 25%. In some effective embodiments the loading of bruceolides according to Formula (1) may be as high as 50%. In other effective embodiments the loading may be between 0.38% and 1%.

When bruceolides according to Formula (1) are loaded into nanoparticles the encapsulation efficiencies may range from 5%-99.9%.

As to further facilitate selective targeting of a disease to be treated the nanoparticle may comprise at least one targeting moiety capable of acting as a ligand to a protein or other molecule expressed by the cancer cell to be treated. The targeting moiety of the nanoparticle therefore may be selected from the group consisting of peptide moieties, carbohydrate moieties, glycoprotein moieties, aptamer moieties, antibodies and folic acid.

As to limit the impact of the cytotoxic agent carried by the nanoparticle when the disease to be treated is a cancer, the targeting moiety may be a ligand for a protein or other molecule selectively and/or overexpressed in the cancer to be treated. Accordingly, the targeting moiety of the nanoparticle may be a ligand for at least one of human epidermal growth factor, prostate specific membrane antigen, nucleolin, sialyl lewis X, cytotoxic T cell antigen-4, tenascin-C, platelet derived growth factor receptor, and pigpen.

The nanoparticle may be formed from polymers comprising any combination of monomers capable of forming nanoparticle such as lactic acid, glycolic acid polyethylene glycol, epsilon caprolactone, and amino acids. The polymers comprising the nanoparticles may be previously formed polymers such as poly (lactide-co-glycolide), polycaprolactone, polylactide, and chitosan. Whether the nanoparticles are formed from preformed polymers, polymers formed form monomers during synthesis of the nanoparticles or any combination thereof, the final polymers incorporated into the nanoparticles may be any combination of natural polymer, synthetic polymers, biodegradable polymers, and polymers that do not trigger an immune response.

Bruceolides according to Formula (1) may be attached to nanoparticles such that at least one of one of $R_1$, $R_2$, $R_3$ and $R_4$ are conjugated to polymers incorporated into the nanoparticle.

In addition to bruceolides according to Formula (1), chemotherapeutic formulations may contain other chemotherapeutic agents such as, but not limited to, chemotherapeutic agents, chemosensitizers, radiosensitizers and any combination thereof. When bruceolides according to Formula (1) are used in combination with chemotherapeutic agents for the treatment of cancer, the chemotherapeutic agent may be cytotoxic against individual cancer cells, bulk tumor cells and/or cancer stem cells. For example, a chemotherapeutic formulation for the treatment of prostate cancer may include a bruceolide according to Formula (1) and docetaxel. When used in conjunctions with other chemotherapeutic agents, bruceolides may exert a synergistic effect as a result of their inhibitory effect on antioxidant mechanisms and pathways.

Formulations comprising bruceolides according to Formula (1) and other chemotherapeutic agents may have both agents carried by nanoparticles. In some formulations, both chemotherapeutic agents may be attached to nanoparticles by site specific cleavable moieties. In other formulations one chemotherapeutic agents may be attached to nanoparticles and the other loaded into nanoparticles. Formulations in which both of the chemotherapeutic agents are loaded into nanoparticles are also possible. In such formulations, the chemotherapeutic agents may be loaded into the same or different nanoparticles and/or attached to the same or different nanoparticles.

Chemotherapeutic agents according to Formula (1) and/or chemotherapeutic formulations comprising a chemotherapeutic agent according to Formula (1) carried by a nanoparticle may be administered intravenously, orally, pulmonary via inhalation, topically, subcutaneously, intramuscularly, and/or intratumorally.

The amount of chemotherapeutic agent and chemotherapeutic formulation administered ideally will provide a concentration of the chemotherapeutic agent according to Formula (1) at the site of tumor of 1 nM to 10,000 nM.

To overcome the potential challenges and facilitate the clinical use of brusatol in the treatment of cancers and other disease states, the fabrication and development of nanoparticle formulations of brusatol may confer significant delivery advantages. First, the transient brusatol effect on Nrf2 can be reversed by a sustained, continuous release from a nanoparticle dosage form thereby ensuring sustained action on Nrf2. Second, the absorption, distribution and elimination of the encapsulated drug molecules in the body are determined by the properties of the nanocarrier and the presence or absence of specific targeting ligands on the nanoparticle surface. Das Neves Jose, Amiji Mansoor M., Bahia Maria Fernanda, Sarmento Bruno, "Nanotechnology-based systems for the treatment and prevention of HIV/AIDS," Advanced Drug Delivery Reviews (2010) 62: 458-477. Thus, delivery in a nanoparticle platform holds the potential to reduce adverse effects and increases therapeutic efficacy as a result of site-specific delivery via active and passive delivery mechanisms (drug targeting). Esmaeili Farnaz, Ghahremani Mohammad Hossein, Ostad Seyed Nasser, Atyabi Fatemeh, Seyedabadi Mohammad, Malekshahi Mazda Rad, Amini Mohsen, Dinarvand Rassoul, "Folate-receptor-targeted delivery of docetaxel nanoparticles prepared by PLGA-PEG-folate conjugate," Journal of Drug Targeting (2008) 16(5): 415-423. Using this approach, the drug is released at the site of action conferring selective toxicity without toxicity to neighboring cells. Nanoparticle drug delivery also allows synchronous delivery of multiple drugs (combination therapy) which is essential to suppress chemoresistance and also improve therapeutic efficacy. Third, formulation in a nanoparticle dosage form also circumvents solubility issues.

These and other aspects may be understood more readily from the following description.

DETAILED DESCRIPTION

Figure 1A:
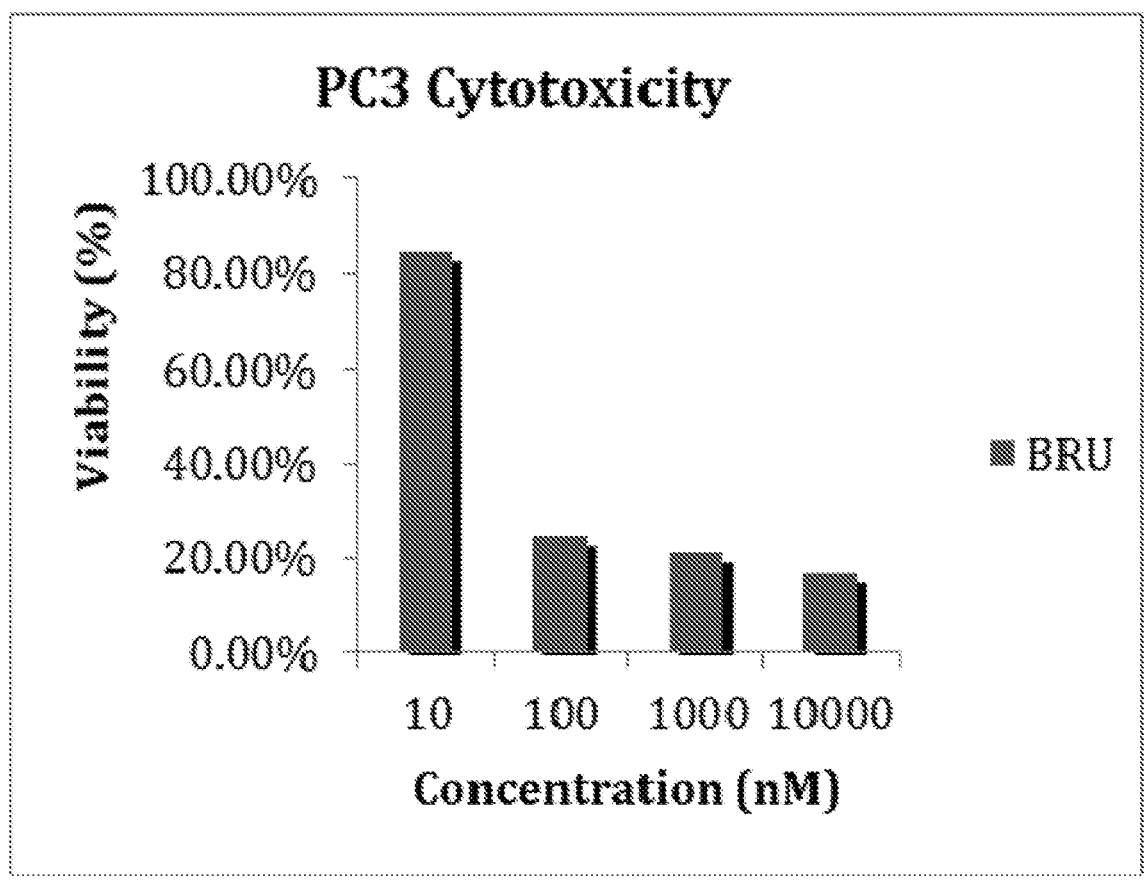
FIGS. 1A and 1B are bar graphs showing the result of cytotoxic studies of different concentrations of brusatol using prostate cancer cell lines.

Chemotherapeutic agents and/or Chemotherapeutic formulations for the treatment of cancer, such as prostate cancer, and other diseases, selectively targeting unwanted cells may be prepared from bruceolides represented by the following formula:

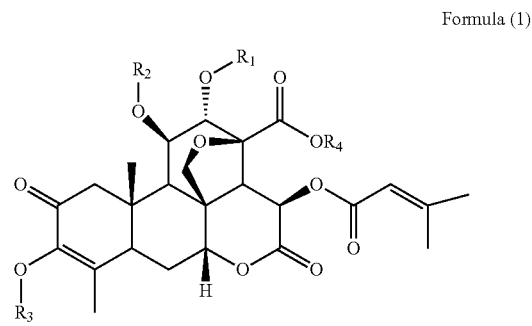

Formula (1)

wherein, $R_1$, $R_2$, $R_3$ and $R_4$ are selected from a site specific cleavable moiety, an alkyl, and a hydrogen. The chemotherapeutic agents and/or chemotherapeutic formulations may be in the form of nanoparticles.

It should be appreciated that "treatment" as used herein is well known in the art. Treatment indicates that a disorder or disease is suspected or has been diagnosed in a subject. Treatment may lead to a halt in the progression of the disorder or disease or a delay in the progression of the disorder or disease. Treatment may also lead to a partial amelioration of symptoms or complete response. Amelioration may, for example, lead to a stop in the progression of the disorder or disease or a delay in the progression of the disorder or disease. Such a partial or complete response may be followed by a relapse.

In some embodiments at least one of $R_1$, $R_2$, $R_3$ and $R_4$ is a site specific cleavable moiety. The site specific cleavable moiety at $R_1$, $R_2$, $R_3$ and/or $R_4$ may inhibit the chemotherapeutic activity of the bruceolide until cleaved, i.e., removed, within and/or near the site of the disease to be treated. Accordingly, a bruceolide according to Formula (1) may be a prodrug of a cytotoxic agent having no or diminished cytotoxic effect until the site specific cleavable moiety is removed.

Site specific cleavable peptide moieties including at least one amino acid residue may be incorporated at $R_1$, $R_2$, and $R_3$ by forming an ester bond between a carboxyl group of the peptide moiety and the corresponding ring of the bruceolide according to Formula (1). By way of non-limiting example, a bruceolide having a hydrogen at any of $R_1$, $R_2$, and $R_3$ may have peptide moiety attached by way of a Fischer Esterification.

Site specific cleavable peptide moieties including at least one amino acid residue may be incorporated at $R_4$ by forming an amide bond between an amine of the peptide moiety and the carboxy late adjacent to $R_4$.

Site specific cleavable moieties at $R_1$, $R_2$, $R_3$ and $R_4$ are not limited to peptide moieties but rather may include any combination of peptide moieties, carbohydrate moieties, glycoprotein moieties and aptamer moieties. Glycoprotein moieties may be attached in a manner similar to that of peptide moieties. Carbohydrate moieties, aptamer moieties and glycoprotein moieties may also be attached at $R_1$, $R_2$, $R_3$ and $R_4$ by a glycosidic linkage. Aptamer moieties may be attached at $R_1$, $R_2$, $R_3$ and $R_4$ by phosphodiester linkage.

Other possible site specific cleavable moieties that may be attached at any of $R_1$, $R_2$, $R_3$ and $R_4$ include monomers, polymers, biopolymers, substrates of proteases and other tumor-specific enzymes, substrates of enzymes or other molecules overexpressed by cancer cells and/or specific to a tumor microenvironment attached, aptamers, antibodies, substrates of PSA, substrates of fibroblast activation protein, substrates of prostate specific membrane antigen, small molecules, folic acid and other such substances that have affinity for sites near and/or within the site of the disease to be treated.

In some embodiments the linker may comprise biotin.

The site specific cleavable moiety at $R_1$, $R_2$, $R_3$ and/or $R_4$ may inhibit the chemotherapeutic activity of the bruceolide until cleaved, i.e., removed, within and/or near the site of the disease to be treated. Accordingly, a bruceolide according to Formula (1) may be a prodrug of a cytotoxic agent having no or diminished cytotoxic effect until the site specific cleavable moiety is removed.

As to selectively transform a prodrug according to Formula (1) into its full cytotoxic form when within and/or near the site of the disease to be treated, the site specific cleavable moiety may be sensitive, i.e., cleavable, by an enzyme expressed by the cancer to be treated. As to lessen the impact of the cytotoxic agent on healthy cells, the enzyme to which the selectively cleavable moiety is sensitive may be selectively expressed in the cancer to be treated. In combination or the alternative, the enzyme to which the selectively cleavable moiety is sensitive may be over expressed in the cancer to be treated. For example, when a bruceolide according to Formula (1) is administered to treat prostate cancer, at least one of $R_1$, $R_2$, $R_3$ and $R_4$ may be a site specific cleavable moiety sensitive to prostate specific antigen. Sensitivity to prostate specific antigen may be imparted by including in at least one of $R_1$, $R_2$, $R_3$ and $R_4$ a peptide moiety comprising a leucine adjacent to a glycine, such as His-Ser-Ser-Lys-Leu-Gln-Leu [SEQ ID NO: 1].

As to facilitate selective delivery to cancer tumors, the composition may be in the form of a nanoparticle. Similarly, in one form, at least one of $R_1$, $R_2$, $R_3$ and $R_4$ in Formula (1) may be a site specific cleavable moiety connected to a nanoparticle. Cancer tumors, as with healthy tissue, forms blood vessels to survive. However the blood vessels formed by cancer tumors are usually abnormal in form and architecture. Often they contain poorly aligned endothelial cells with wide fenestrations and lack a smooth muscle layer. As a result of these abnormalities, the blood vessels of tumors cells contain gaps into which nanoparticles may settle. As such gaps are less prevalent in healthy tissue, nanoparticles may selectively settle within tumors thereby facilitating selective drug delivery. Accordingly, attaching bruceolides according to Formula (1) to nanoparticles and/or loading bruceolides according to Formula (1) into nanoparticles allows for a selective targeting of cancer cells. Nanoparticles carrying bruceolides according to Formula (1) may between 50 nm and 800 nm in diameter and in some cases between about 50 nm and about 250 nm. Bruceolides according to Formula (1) may also be carried by nanoparticles between 250 nm and 315 nm in diameter. Nanoparticles as large as 800 nm in diameter may also be used to carry bruceolides according to Formula (1).

Bruceolides according to Formula (1) may be attached to nanoparticles such that at least one of one of $R_1$, $R_2$, $R_3$ and $R_4$ are conjugate to polymers incorporated into the nanoparticle. In some embodiments the nanoparticle may comprise a reactive functional group that can form a covalent bond with a selectively cleavable moiety at any of $R_1$, $R_2$, $R_3$ and $R_4$, such as a carboxyl-, amino-, hydroxyl, azide, and/or alkyne. In some embodiments, a bruceolide according to Formula (1) may be attached to monomers and/or polymers comprising a nanoparticle prior to formation of the nanoparticle.

In combination or the alternative, bruceolides according to Formula (1) may be loaded into the nanoparticles. When bruceolides according to Formula (1) are loaded into nanoparticles, the loading may be between 0.1% and 50%. Effective embodiments may also include loadings between 0.2% and 25%. In some effective embodiments the loading of bruceolides according to Formula (1) may be as high as 50%. In other effective embodiments the loading may between 0.38% and 1%.

Various nanoparticles may be used to carry bruceolides according to Formula (1) such as liposomes, polymeric nanoparticles, dendrimers, inorganic nanoparticles and/or polymeric micelles. Likewise, nanoparticles used to carry bruceolides according to Formula (1) may be synthesized from a variety of molecules including preformed polymers, monomers, macromonomers, albumin and/or lipids.

In some embodiments that nanoparticles may be formed from polymers that do not elicit an immune response.

Nanoparticles carrying bruceolides according to Formula (1), in some embodiments, may be stealth particles comprising a core in which a bruceolide according to Formula (1) is encapsulated and a corona having a material that allows the nanoparticle to evade the activity of the cells of the reticuloendothelial system, such as a hydrophilic neutral material. The corona of such a stealth nanoparticle may be linked to a targeting moiety. In some embodiment of stealth nanoparticles the corona may comprise polyethylene glycol or functionalized polyethylene glycol.

In some embodiments, nanoparticle loaded with bruceolides according to Formula (1) may be prepared by dissolving monomers or polymers in an organic solvent. When prepared using polymers, the polymers may have a molecular weight between 2,000 and 200,000 Daltons as determined by gel permeation chromatography. In some embodiments, nanoparticles may be formed from polymers having a molecular weight between 5,000 and 75,000 Daltons as determined by gel permeation chromatography.

The solvent may be any solvent capable of dissolving the monomers and polymers utilized to form the nanoparticles. Possible solvents include dichloromethane, ethyl acetate, chloroform, acetonitrile, DMSO, and/or acetone.

As a non-limiting example, 50 mg of mPEG-Poly (lactide-co-glycolide) (lactic acid:glycolic acid 1:1) may be dissolved in dichloromethane/ethyl acetate.

To the monomer mixture, a bruceolide according to Formula (1) dissolved in solvent is added. The solvent used to dissolve the bruceolide may be any organic solvent capable of dissolving the bruceolide such as 1 to 4 mixture of DMSO and acetone.

An aqueous phase is then added to the bruceolide-monomer mixture. The aqueous phase may be any compatible aqueous phase with or without a stabilizer such as polyvinyl alcohol.

Figure 7:
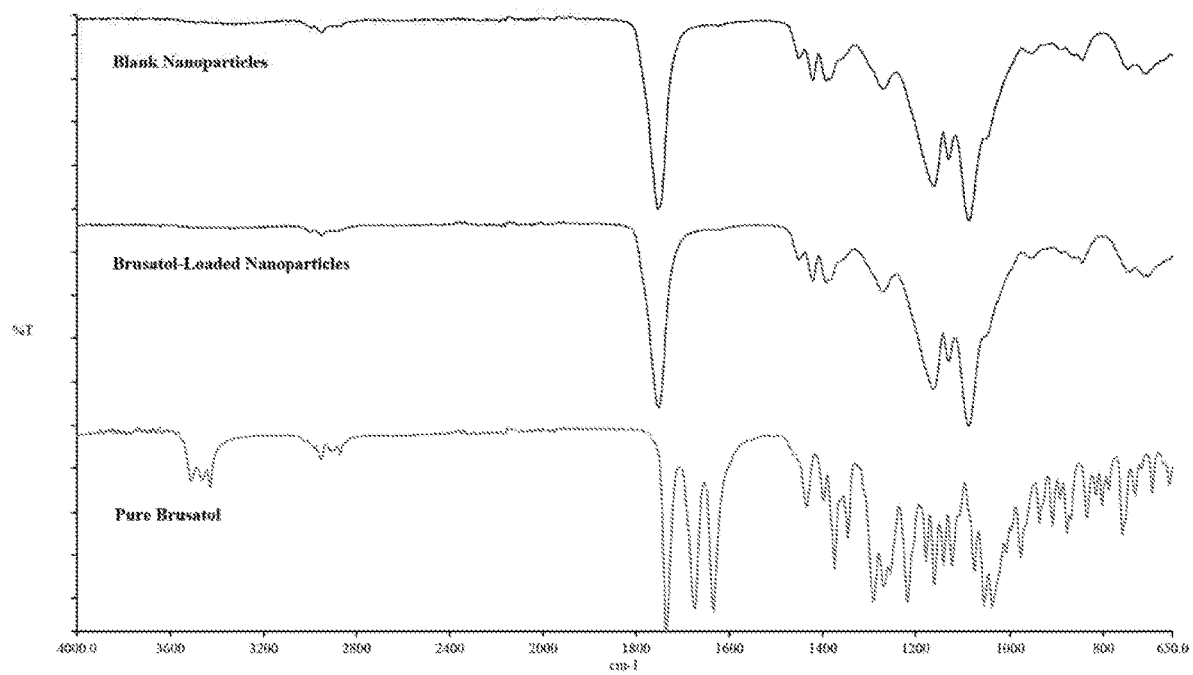
FIG. 7 shows Fourier transform infrared spectroscopy data. (a) Blank nanoparticles (top), (b) brusatol-loaded nanoparticles (middle), (c) pure brusatol (bottom).

The inner organic phases may then be emulsified in the aqueous phase with high intensity sonication. Nanoparticles loaded with the bruceolide according to Formula (1) may then be precipitated by evaporating the solvent. The resulting nanoparticle suspension may then be washed via vortexing the particles in deionized water followed by centrifugation three times. After the final centrifugation, the nanoparticle suspension may be flash-frozen over liquid nitrogen and lyophilized for 48 hours.

As to further facilitate selective targeting of a tumor to be treated the nanoparticle may comprise at least one targeting moiety capable of acting as a ligand to a protein or other molecule expressed by in and/or near the site of the disease to be treated. The targeting moiety of the nanoparticle therefore may be selected from the group consisting of peptide moieties, carbohydrate moieties, glycoprotein moieties, aptamer moieties, small molecules and antibodies. In some embodiments, the targeting moiety of the nanoparticle may be a ligand for at least molecule expressed by cancer cells, such as one of human epidermal growth factor, prostate specific membrane antigen, nucleolin, sialyl lewis X, cytotoxic T cell antigen-4, tenascin-C, platelet derived growth factor receptor, and pigpen.

In addition to bruceolides according to Formula (1), chemotherapeutic formulations may contain other chemotherapeutic agents, such as but not limited to docetaxel and the like.

When used in conjunctions with other chemotherapeutic agents, bruceolides may exert a synergistic effect as a result of a result of inhibiting antioxidant mechanism and/or other pathways. Formulations comprising bruceolides according to Formula (1) and other chemo-therapeutic agents may have both agents carried by nanoparticles. In some formulations, both chemotherapeutic agents may be attached to nanoparticles by site specific cleavable moieties. In other formulations one chemotherapeutic agent may be attached to nanoparticles and the other loaded into nanoparticles. Formulations in which both of the chemotherapeutic agents are loaded into nanoparticles are also possible. In such formulations, the chemotherapeutic agents may be loaded into the same or different nanoparticles and/or attached to the same or different nanoparticles.

Chemotherapeutic agents according to Formula (1) and/or chemotherapeutic formulations comprising a chemotherapeutic agent according to Formula (1) carried by a nanoparticle may be administered intravenously, orally, pulmonary via inhalation, topically, subcutaneously, intramuscularly, and intratumorally. The amount of chemotherapeutic agent and/or chemotherapeutic formulation administered ideally will provide a concentration of the chemotherapeutic agent according to Formula (1) at the site of tumor of 1 nM to 10,000 nM.

EXAMPLE 1

Brusatol Treatment of Prostate Cancer

Due to its mechanism of action as a protein synthesis inhibitor, the inventor conducted an investigation into the efficacy of brusatol to inhibit prostate cancer cell line synthesis. Prostate cancer lines PC3 and LNCaP were cultivated in the presence of 1 nM, 100 nM, 1,000 nM and 10,000 nM concentrations of brusatol and 0.1% DMSO as a control. The results of the investigation are shown in FIG. 1. As can be seen from FIG. 1, the results of the investigation indicate that brusatol kills prostate cancer cells with an $IC_{50}$ between 1 nM and 100 nM.

EXAMPLE 2

Brusatol Loaded Nanoparticles

Brusatol loaded nanoparticle may be prepared by dissolving 50 mg of mPEG-Poly (lactide-co-glycolide) (lactic acid: glycolic acid 1:1) in dichloromethane or ethyl acetate. An organic phase may then be formed by adding to the PLGA solution a solution of brusatol dissolved in a mixture of DMSO:Acetone (1:4). An aqueous phase comprising a polyvinyl alcohol solution is then added. The organic phase is then emulsified in the aqueous phase by high intensity sonication. Following sonication, particles are precipitated by solvent evaporation. The particle suspension thus obtained is then washed by vortexing the particles in deionized water followed by centrifugation three times. After which, the nanoparticle suspension was flash-frozen over liquid nitrogen and lyophilized for 48 hours.

The surface morphology of the nanoparticles obtained may be evaluated using a scanning electron microscope. To evaluate surface morphology of the produced nanoparticles, the obtained nanoparticle suspension in distilled water may be placed on a carbon tape affixed to a specimen stub and dried in vacuo. The dried nanoparticles may then be gold-coated and viewed using the scanning electron microscope.

FIG. 2 is a scanning electron micrograph of brusatol loaded nanoparticles produced and imaged as detailed above. As shown in FIG. 2, the brusatol loaded nanoparticles are smooth and spherical.

The size of nanoparticles may be determined by dynamic light scattering at 25° C. Prior to dynamic light scattering, the obtained nanoparticle suspension may be filtered through a 5 μm syringe filter.

FIG. 3 shows particle size analysis given by the polydispersity index of the brusatol loaded nanoparticles obtained as detailed above. In one form, the mean effective diameter obtained for the blank nanoparticle formulation was 267.8±3.7 nm. In one form, after loading with brusatol, the mean effective diameter increased to 309.23±2.3 nm. The polydispersity is an indication of the size distribution of nanoparticle formulations. Data obtained for blank and brusatol-loaded nanoparticles show that, in one form, the polydispersity is 0.143±0.051 and 0.178±0.098, respectively.

Drug loading, i.e., the weight percent of brusatol in the nanoparticles, may be quantified by HPLC from standard calibration curves of pure brusatol. A known amount of the freeze-dried nanoparticles obtained may be dissolved in acetonitrile. The resulting solution may then be filtered through a 0.22 μm syringe filter. The amount of brusatol dissolved in the solution may then be quantified by HPLC using a mobile phase of 0.05% v/v phosphoric acid:acetonitrile (60:40) at a flow rate of 1 mL/min and using a diode array detector at 235 nm.

Brusatol loaded nanoparticles obtained as detailed above had a percent drug loading of 1%. FT-IR studies reveal that the drug loading determined was due to encapsulated drug and not due to drug adsorbing to the surface of the nanoparticles (FIG. 7). The spectrum obtained for blank nanoparticles is similar to that for drug-loaded nanoparticles and no visible brusatol peak was visible in the spectrum of the drug-loaded nanoparticles.

EXAMPLE 3

Brusatol and Docetaxel Loaded Nanoparticles

Brusatol and docetaxel loaded nanoparticle may be prepared by dissolving 50 mg of mPEG-Poly (lactide-co-glycolide) (lactic acid:glycolic acid 1:1) in dichloromethane or ethyl acetate. An organic phase may then be formed by adding to the PLGA solution a solution of brusatol and docetaxel dissolved in a mixture of DMSO:Acetorte (1:4). An aqueous phase comprising a polyvinyl alcohol solution is then added. The organic phase is then emulsified in the aqueous phase by high intensity sonication. Following sonication, particles are precipitated by solvent evaporation. The particle suspension thus obtained is then washed by vortexing the particles in deionized water followed by centrifugation three times. After which, the nanoparticle suspension was flash-frozen over liquid nitrogen and lyophilized for 48 hours.

The surface morphology of the nanoparticles obtained may be evaluated using a scanning electron microscope. To evaluate surface morphology of the produced nanoparticles, the obtained nanoparticle suspension in distilled water may be placed on a carbon tape affixed to a specimen stub and dried in vacuo. The dried nanoparticles may then be gold-coated and viewed using the scanning electron microscope.

Figure 4:
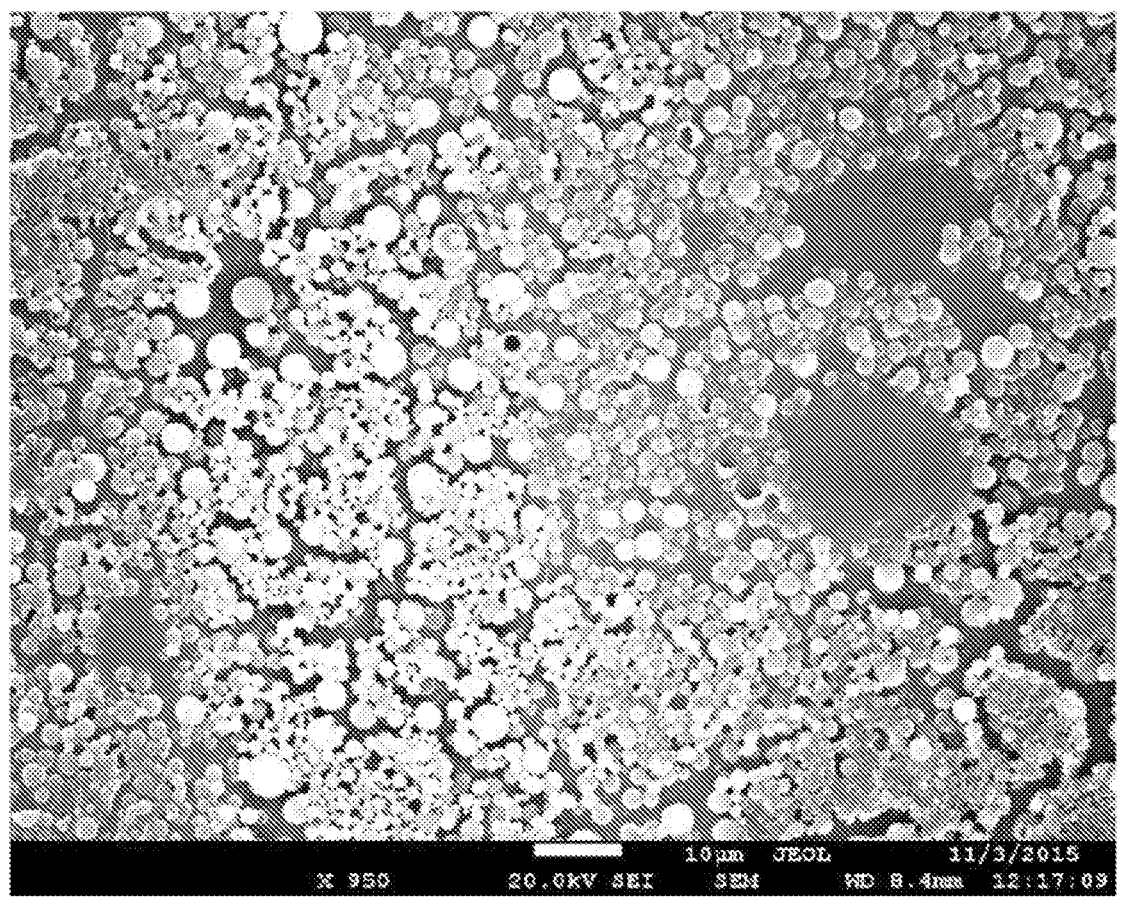
FIG. 4 is a scanning electron micrograph of brusatol and docetaxel loaded nanoparticles.

FIG. 4 is a scanning electron micrograph of brusatol and docetaxel loaded nanoparticles produced and imaged as detailed above. As shown in FIG. 4, the brusatol and docetaxel loaded nanoparticles are smooth and spherical.

The size of nanoparticles may be determined by dynamic light scattering at 25° C. Prior to dynamic light scattering, the obtained nanoparticle suspension may be filtered through a 5 µM syringe filter.

Figure 5:
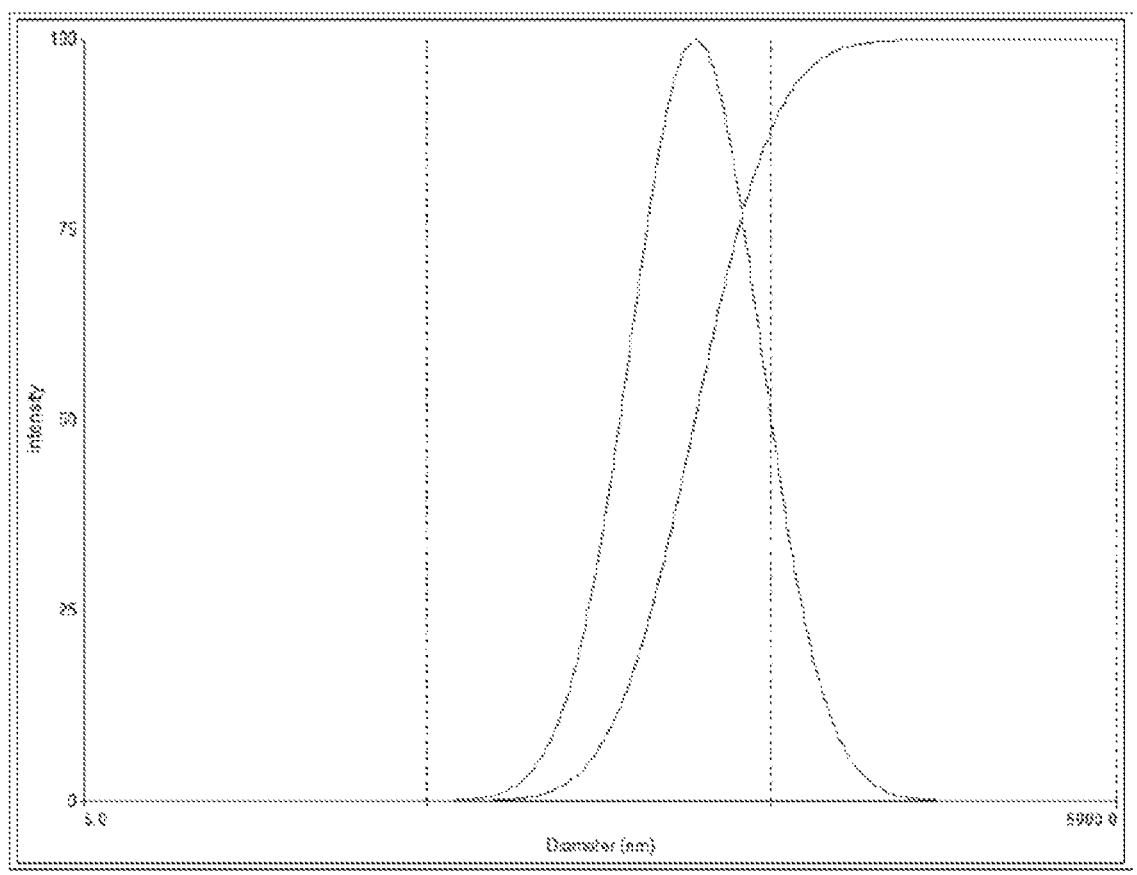
FIG. 5 shows particle size analysis of brusatol and docetaxel loaded nanoparticles.

FIG. 5 shows particle size analysis given by the polydispersity index of the brusatol and docetaxel loaded nanoparticles obtained as detailed above. As shown in FIG. 5, the average particle size of the brusatol and docetaxel loaded nanoparticles was 300±1.4 nm.

Drug loading, i.e., the weight percent of brusatol and docetaxel in the nanoparticles, may be quantified by HPLC from standard calibration curves of pure brusatol and docetaxel. A known amount of the freeze-dried nanoparticles obtained may be dissolved in acetonitrile. The resulting solution may then be filtered through a 0.22 µm syringe filter. The amount of brusatol dissolved in the solution may then be quantified by HPLC using a mobile phase of 0.05% v/v phosphoric acid:acetonitrile (60:40) at a flow rate of 1 mL/min and using a diode array detector at 235 nm. The amount of docetaxel dissolved in the solution may then be quantified by HPLC using a mobile phase acetonitrile:water (50:50) at a flow rate of 1 mL/min and using a diode array detector at 230 nm.

Brusatol and docetaxel loaded nanoparticles obtained as detailed above had a brusatol percent drug loading of 0.38% and a docetaxel percent drug loading of 4.14%.

EXAMPLE 4

Methoxy-terminated polyethylene glycol-poly (lactide-co-glycolide) (mPEG-PLGA) (lactic acid:glycolic acid 1:1) was purchased from Polyscitech® (Akina Inc., West Lafayette, IN, USA). Polyvinyl alcohol (PVA 99-100%, MW 86,000) was purchased from ACROS Organics (Morris Plains, NJ, USA). Brusatol was purchased from carbosynth (San Diego, CA, USA). All other solvents were purchased from Sigma-Aldrich (St. Louis, MO, USA).

Preparation of Nanoparticles

The oil-in-water (o/w) emulsification solvent diffusion method was modified to prepare the nanoparticles. Niwa T., Takeuchi H., Hino T., Kunou N., Kawashima Y, "Preparations of biodegradable nanospheres of water-soluble and insoluble drugs with D, L-lactide/glycolide copolymer by a novel spontaneous emulsification solvent diffusion method, and the drug release behavior," Journal of Controlled Release, (1993) 25(1-2): 89-98. Farnaz et al., p. 415-423. Song Xiangrong, Zhao Yu, Wu Wenbin, Bi Yueqi, Cai Zheng, Chen Qiuhong, Li Yuanbo, Hou Shixiang, "PLGA nanoparticles simultaneously loaded with vincristine sulfate and verapamil hydrochloride: Systematic study of particle size and drug entrapment efficiency," International Journal of Pharmaceutics, (2008) 350: 320-329. The method to encapsulate drugs with wide-ranging solubilities can use different solvents. Using this method 50 mg of mPEG-PLGA was dissolved in dichloromethane or ethyl acetate. Brusatol was dissolved in a mixture of dimethyl sulfoxide: acetone (1:4) and added to the PLGA solution to form the organic phase. The aqueous phase used was polyvinyl alcohol solution (1% w/v). High intensity sonication was used to emulsify the organic phase in the aqueous phase followed by solvent evaporation to precipitate the particles. The nanoparticle suspension was washed in deionized water followed by centrifugation. This was repeated three times. After the final centrifugation step, the nanoparticle suspension was flash-frozen over liquid nitrogen and lyophilized for 48 hours.

Particle Size and Size Distribution Analysis

Particle size and size distribution of nanoparticles was determined by dynamic light scattering (DLS) using 90 Plus particle size analyzer (Brookhaven Instruments Corp., NY, USA). Before analysis, the dilute nanoparticle suspension was filtered through a syringe filter with 5 µm pore size. Particle size was determined at 25° C. The mean of three measurements was recorded. The particle size distribution is given by the polydispersity index (PDI).

Determination of Drug Content of Encapsulated Drug

Drug loading, defined as the weight percent of each drug in the nanoparticle formulation, was determined. The amount of brusatol in the nanoparticles was quantified by a HPLC method from standard calibration curves of pure drug. Briefly, a known amount of freeze-dried nanoparticles was dissolved in acetonitrile. The solution was then filtered through a 0.22 µm syringe filter and the amount of drug dissolved in the solution was quantified using a validated HPLC method on Agilent series 1100 HPLC equipped with a Zorbax Eclipse Plus C18 column kept at 37° C. The mobile phase for HPLC studies is 0.05% v/v phosphoric acid: acetonitrile (60:40) at a flow rate of 1 mL/min. Quantitation of brusatol was carried out using a diode array detector at 235 nm.

The percent drug loading for each drug was calculated from the equation below:

$$\text{Drug loading (\%)} = \frac{\text{Mass of drug nanoparticles}}{\text{Mass of nanoparticles}} \times 100\%$$

Scanning Electron Microscopy (SEM) of Nanoparticles

The surface morphology of the nanoparticles was evaluated using a JSM-7600F Scanning electron microscope (JEOL USA, Inc. Peabody, MA). To evaluate surface morphology, nanoparticle suspension in distilled water was placed on a carbon tape affixed to a specimen stub and dried in vacuo. After drying, the samples were gold-coated prior to viewing. Images were taken at different sample magnifications.

Infrared Spectroscopy Studies

Infrared spectroscopy studies were carried out using a Spectrum 100 Fourier transform infrared (FT-IR) spectrophotometer (Perkin Elmer, Shelton, CT, USA). FT-IR spectra were obtained for brusatol, brusatol-loaded nanoparticles and blank nanoparticles in attenuation total reflectance (ATR) mode and overlaid.

Determination of Brusatol Release Profile

The release profile was determined using a modified published method. Ogunwuyi O., Adesina S., Akala E. O., "D-Optimal mixture experimental design for stealth biodegradable crosslinked docetaxel-loaded poly-ε-caprolactone nanoparticles manufactured by dispersion polymerization," Pharmazie, (2015) 70: 165-176. Briefly, brusatol-loaded nanoparticles were dispersed in 2 mL of phosphate buffered saline (PBS) and placed in a dialysis bag (molecular weight cut off of 12,000-14,000). The dialysis bag was then immersed in a 15 mL Eppendorf tube containing a known amount of PBS. The tube was clamped to a Labquake shaker rotated at 360° and maintained at 37° C. At different time intervals, an aliquot of the release medium was taken and replaced with fresh PBS to maintain sink conditions. The sample was diluted with acetonitrile and filtered through a 0.22 µm syringe filter and the amount of brusatol released into the solution was quantified by HPLC using the validated HPLC method.

Cell Cultures

The human prostate cancer cell lines, PC3 and LNCaP, were obtained from American Type Culture Collection (Manassas, VA). The PC3 and LNCaP cell lines were maintained in RPMI 1640 supplemented with 10% (v/v) FBS and 100 U/mL of penicillin G and 100 g/mL of streptomycin sulfate. The cells were maintained as a monolayer in an incubator at 37° C. in a humid atmosphere with 5% CO2.

Cytotoxicity Studies

PC3 (seeding density of 3,000 cells per well) and LNCaP (seeding density of 6,000 cells per well) were seeded in 96-well plates and allowed to attach for 24 h. Cells were then treated with 100 µL of culture medium containing brusatol-loaded nanoparticles or brusatol in solution (to prepare the control brusatol solution, brusatol concentrations of 500 µM, 100 µM, 50 µM and 10 µL were prepared as stock solutions in sterile DMSO. Serial 1000-fold dilutions of these stock solutions were then prepared in RPMI to give growth media with drug concentrations of 500 nM, 100 nM, 50 nM and 10 nM respectively each containing 0.1% DMSO. To allow direct comparison, the amount of brusatol-loaded nanoparticles containing the same amount of brusatol as the brusatol solution was used. Control cells were treated with culture medium only, culture medium with 0.1% DMSO and culture medium containing blank nanoparticles of the same quantity expected to produce the precalculate concentrations of brusatol. Cell viability was assessed at 120 h after treatment. The Cell Titer 96® Non-Radioactive Cell Proliferation Assay manufactured by Promega Corporation was employed for this study. Results are presented as percent viability normalized to controls and represent the mean±SD of six replicates per concentration tested. Results were analyzed using One-way Analysis of Variance (ANOVA) and Student's t-test with the aid of SPSS® statistical software. Differences were considered significant at $p<0.05$.

Cell Cycle Experiments

LNCaP cells (seeding density of 40,000 cells per well) were seeded in triplicates in a 24-well plate and incubated for 48 hours. Cells were treated with 1 mL of 50 nM brusatol solution for 120 h and control cells were treated with 1 mL of culture media containing 0.01% DMSO. The experiment was done in triplicate. At the 120 h time point, cells were harvested and washed twice with cold PBS, fixed in 70% ethanol for 1 h at 4° C. The cells were then washed twice with PBS, and treated with ribonuclease followed by staining with propidium iodide. The stained cells were subjected to cell cycle analysis using the BD Accuri™ C6 flow cytometer (BD Biosciences, Ann Arbor, MI, USA). For each replicate, 20,000 events were recorded.

In Vitro Intracellular Nanoparticle Localization

Cellular uptake of fluorescent nanoparticles was investigated using spinning-disk confocal microscopy. PC3 cells (10,000 cells/well) were seeded in a 24 well plate containing coverslips. After 24 hours, the media was aspirated and replaced with fresh media containing 50 µg/ml of rhodamine-123-labeled nanoparticles and incubated for 6 hours. The cells were washed 4 times with PBS to remove nanoparticles that were not internalized followed by membrane staining with CellMask Deep Red plasma membrane stain (4 µg/mL) for 15 min. The cells were washed twice with PBS and fixed with 4% paraformaldehyde for 20 min followed by DAPI (0.08 µg/mL) staining of chromosomal DNA for 10 min. Fluorescent images of fixed samples were captured using a Nikon Eclipse Ti microscope equipped with a 60×1.4NA Plan Apo Lamda objective. Fluorescent signals of DAPI, rhodamine-123 and CellMask Deep Red were collected after excitation with 405-, 488- and 640 nm laser lines respectively. Images were acquired using NIS-Elements software.

Figure 1B:
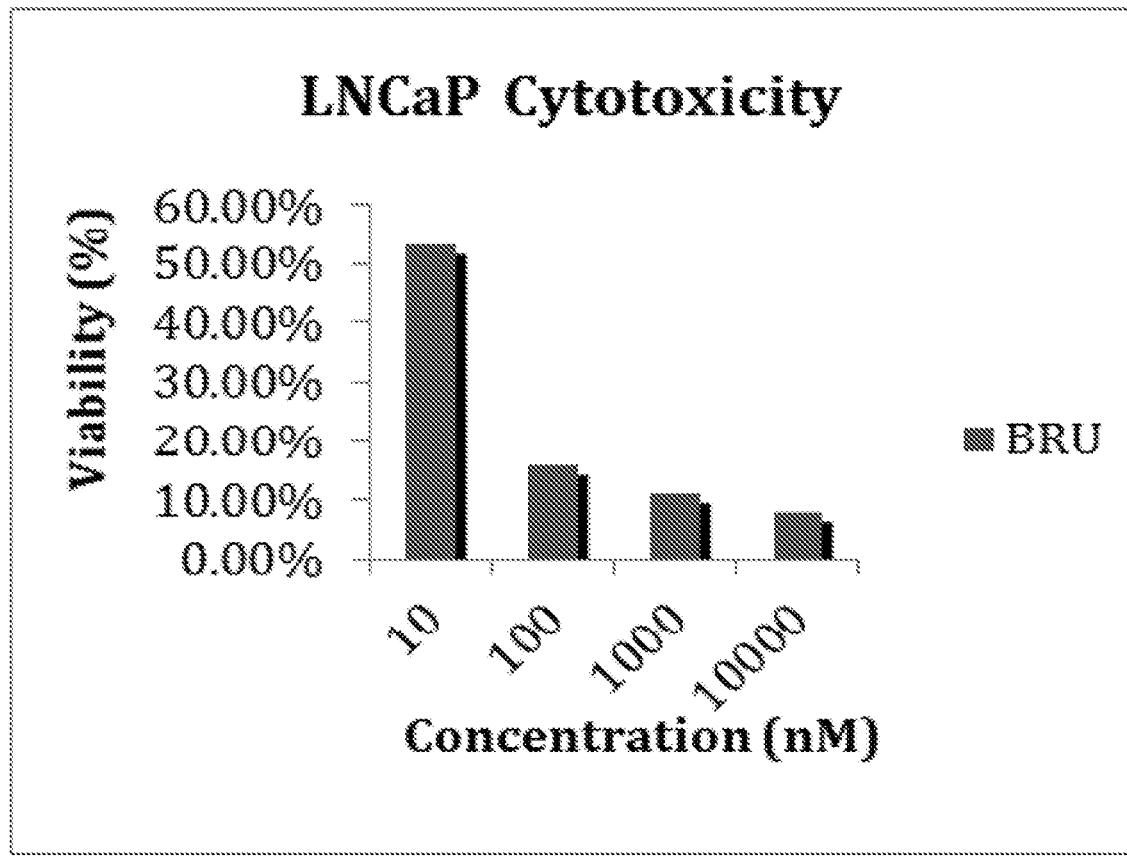
Figure 2:
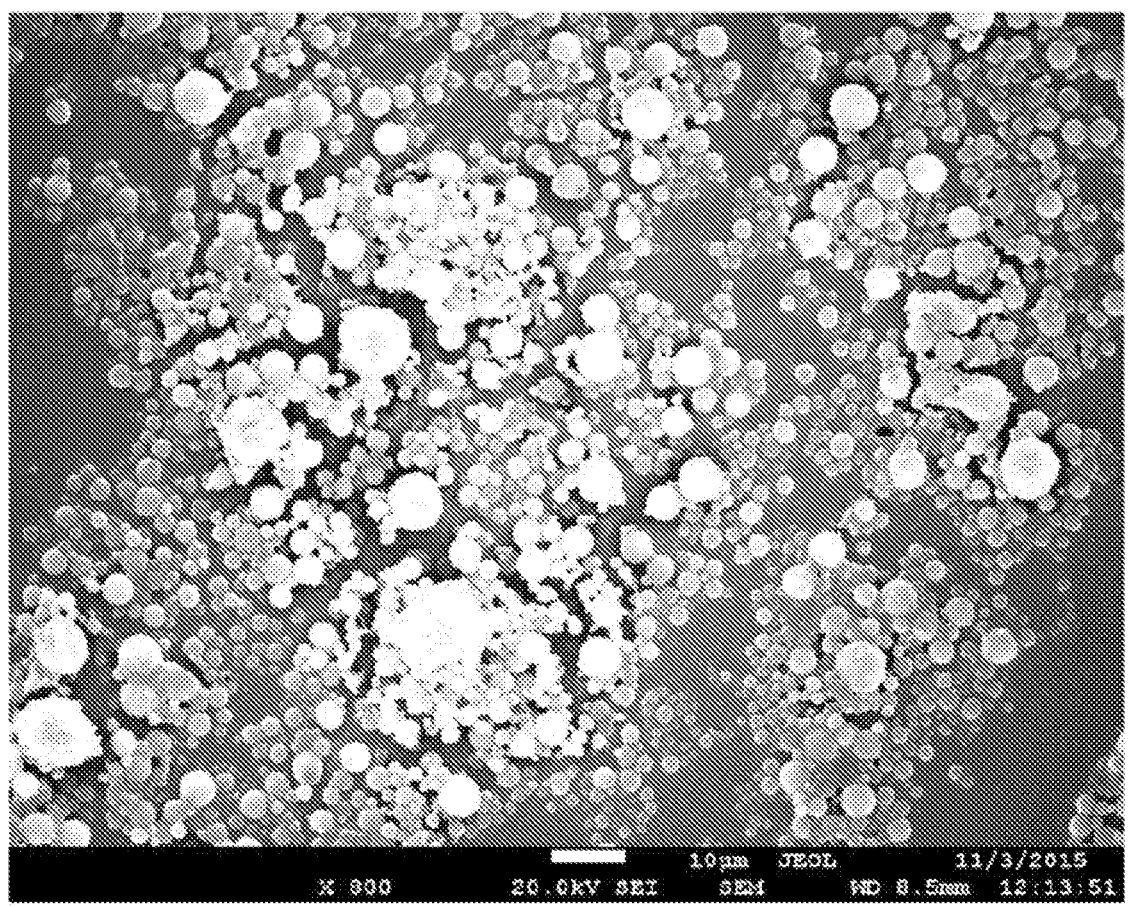
FIG. 2 is a scanning electron micrograph of brusatol loaded nanoparticles.
Figure 3:
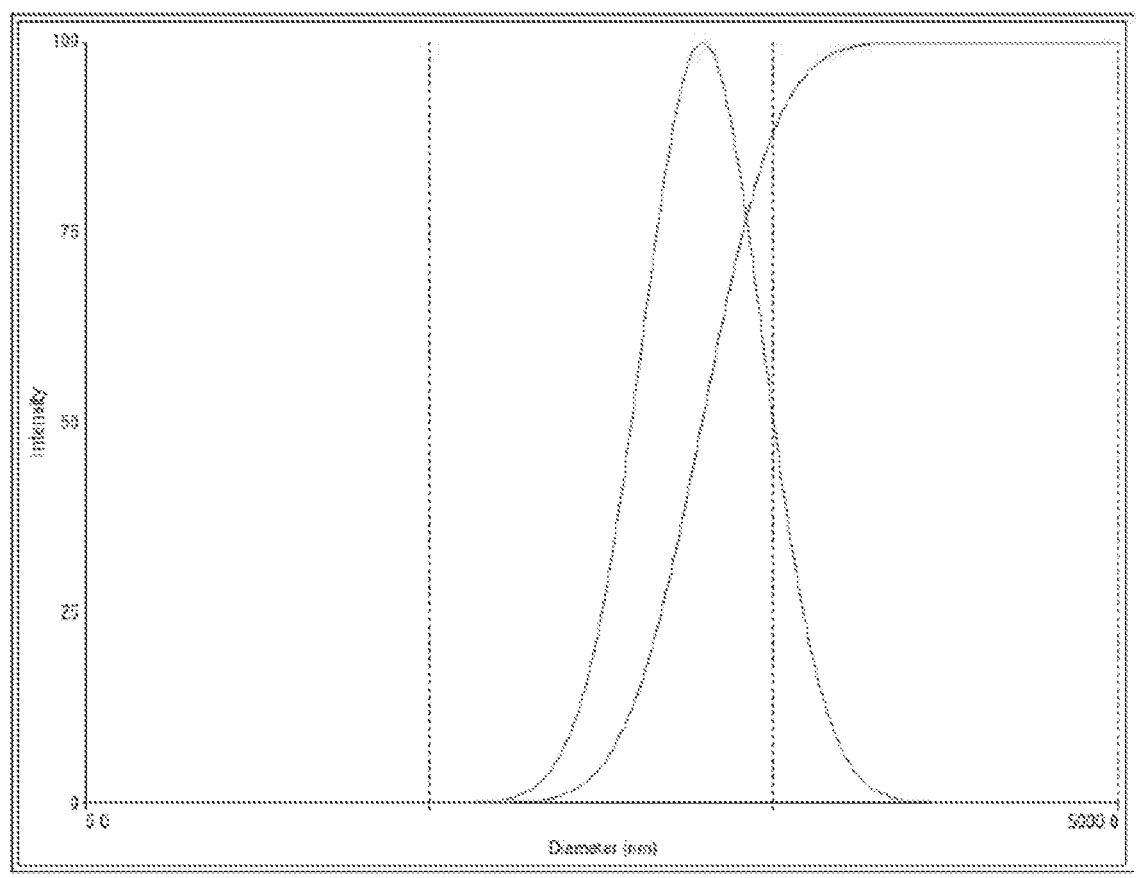
FIG. 3 shows particle size analysis of the brusatol loaded nanoparticles.

Preliminary cytotoxicity study carried out using a broad range of concentrations of brusatol solution on PC3 and LNCaP cell lines over 72 hours revealed toxicity to both prostate cancer cell lines. Data showed impressive killing of these cancer cells (FIG. 1).

Figure 6:
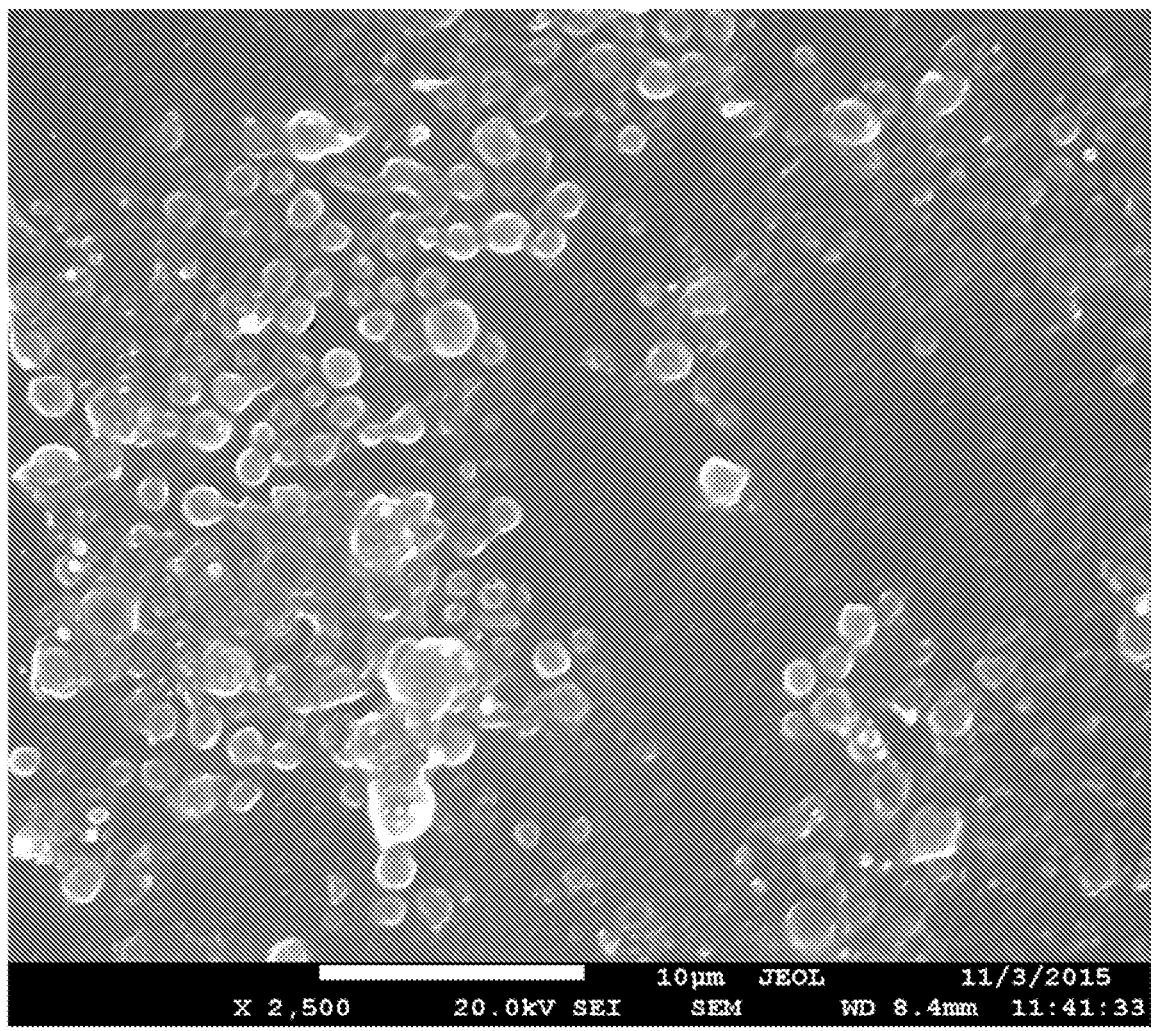
FIG. 6 shows a representative SEM micrograph of brusatol-loaded nanoparticles.

Based on the degree of cytotoxicity displayed in the prostate cancer cell lines used, and the reported non-selective mechanism of action, brusatol-loaded nanoparticles for site-specific delivery of brusatol have been prepared. A solvent system has also been developed that permits dissolving multiple drugs with varying solubilities in different solvents. The solvent system can be used to prepare blank and brusatol-loaded nanoparticles using the oil-in-water (O/W) emulsification solvent diffusion method. Scanning electron microscopy revealed the formation of smooth spherical nanoparticles (FIG. 6).

Figure 8:
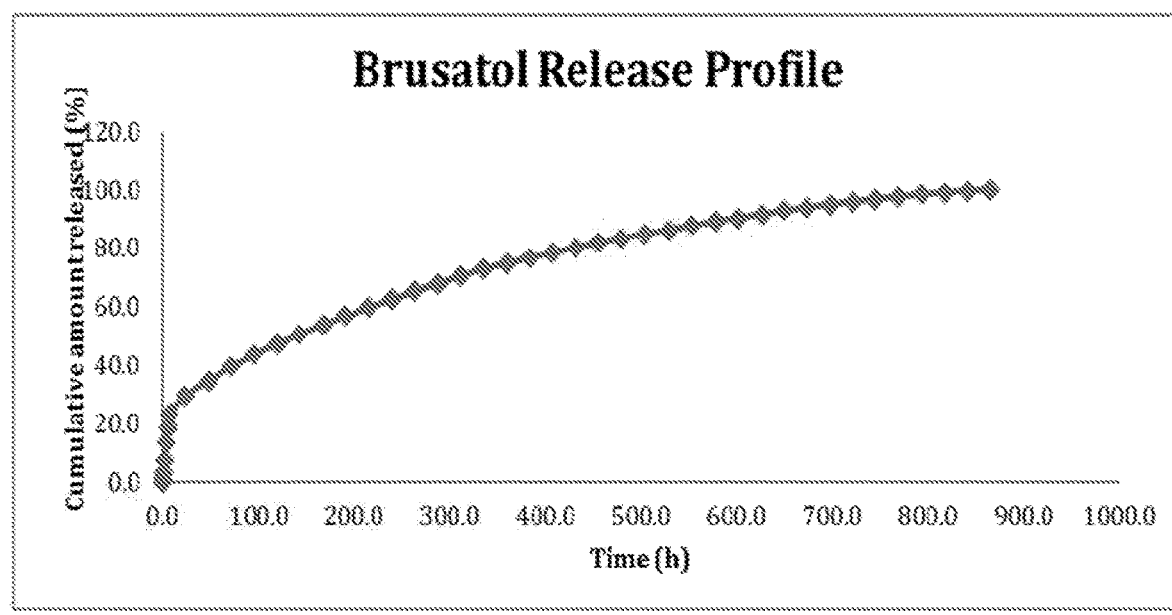
FIG. 8 shows in vitro release isotherm for brusatol-loaded PLGA-PEG nanoparticles in PBS at 37° C. Standard deviation (1.46%-8.13%; n=3).

The in vitro release of brusatol from brusatol-loaded PLGA-PEG nanoparticles was evaluated by a dialysis method in phosphate buffered saline maintained at 37° C. in a laboratory oven using a Labquake shaker. The in vitro release isotherm show sustained release of the encapsulated drug over 866 hours (36 days) with less than 30% of the drug payload released in 24 hours and about 50% released in 144 hours (FIG. 8). In addition, the release was biphasic with an initial burst release followed by a period of gradual release.

It has been reported that polymer coating of a nanoparticle acts as a drug release barrier and consequently impacts drug release. Singh Rajesh, Lillard Jr. James W., "Nanoparticle-based targeted drug delivery," Experimental and Molecular Pathology, (2009) 86: 215-223. Generally, the burst release is attributed to dissolution and the subsequent diffusion of poorly entrapped drug in the polymer matrix while the more sustained release is governed by diffusion and matrix erosion from the PLGA core (Danhier et al., 2009; Adesina et al., 2014, Ogunwuyi et al., 2015; Singh and Lillard, 2009). Ogunwuyi O., Adesina S., Akala E. O., "D-Optimal mixture experimental design for stealth biodegradable crosslinked docetaxel-loaded poly-ε-caprolactone nanoparticles manufactured by dispersion polymerization," Pharmazie, (2015) 70: 165-176. The observed sustained release of brusatol from the nanoparticle is advantageous to ensure a sustained action on Nrf2 and thus counteract its reported transient effect.

Figure 9A:
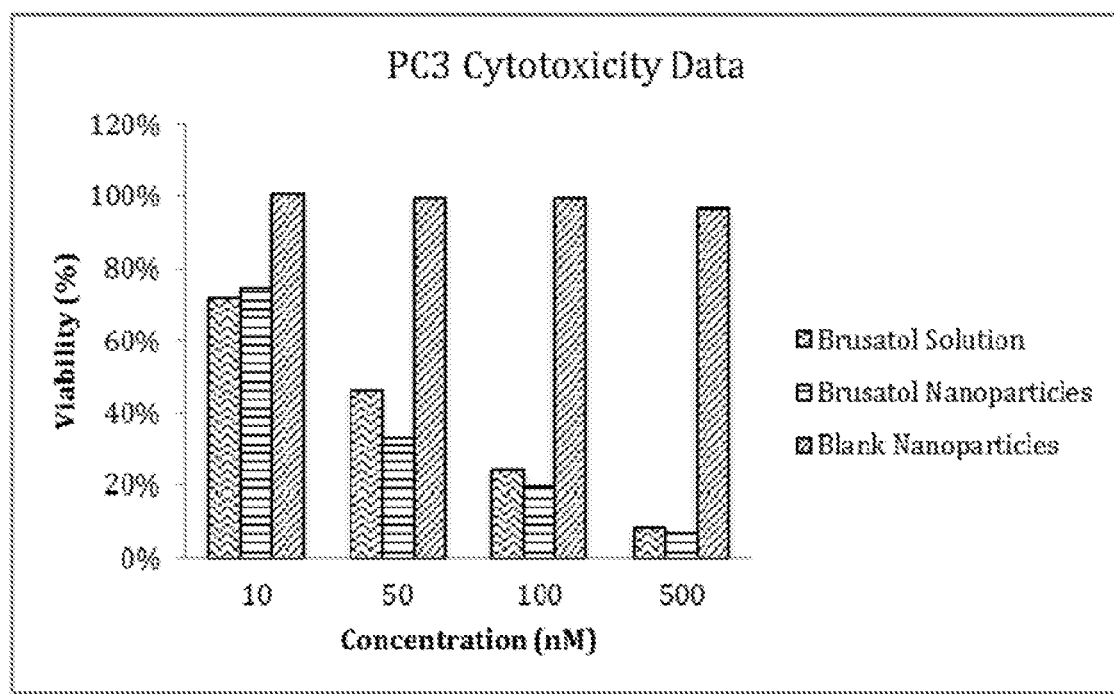
FIGS. 9A and 9B are bar graphs showing the evaluation of cytotoxicity of brusatol solution, brusatol-loaded nanoparticles and blank nanoparticles using the Cell Titer 96® Non-Radioactive Cell Proliferation Assay at 120 hours. (a) PC3 cells (top), (b) LNCaP cells (bottom).
Figure 9B:
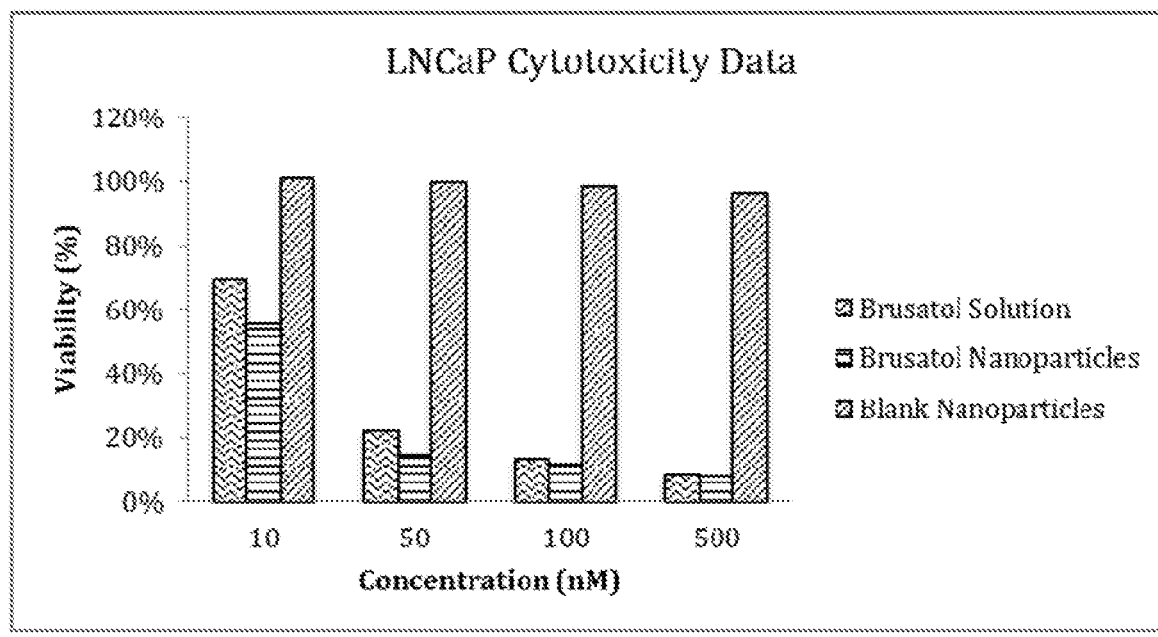

The data obtained from evaluation of toxicity of the blank nanoparticle formulation shows that the blank nanoparticles were not toxic at the highest concentration tested which is equivalent to the amount of polymer in 500 nM of brusatol-loaded nanoparticles. Percent viability values of greater than 95% was obtained for all the concentrations tested. In addition, cytotoxicity data reveal that both brusatol-loaded nanoparticles and the control brusatol solutions at the same concentrations exhibited dose-dependent toxicity to PC3 and LNCaP prostate cancer cell lines at the concentrations used in this study at 120 hours (FIGS. 9A and 9B). Generally, the nanoparticle formulation showed more toxicity to both cell lines compared to brusatol solution.

Figure 10:
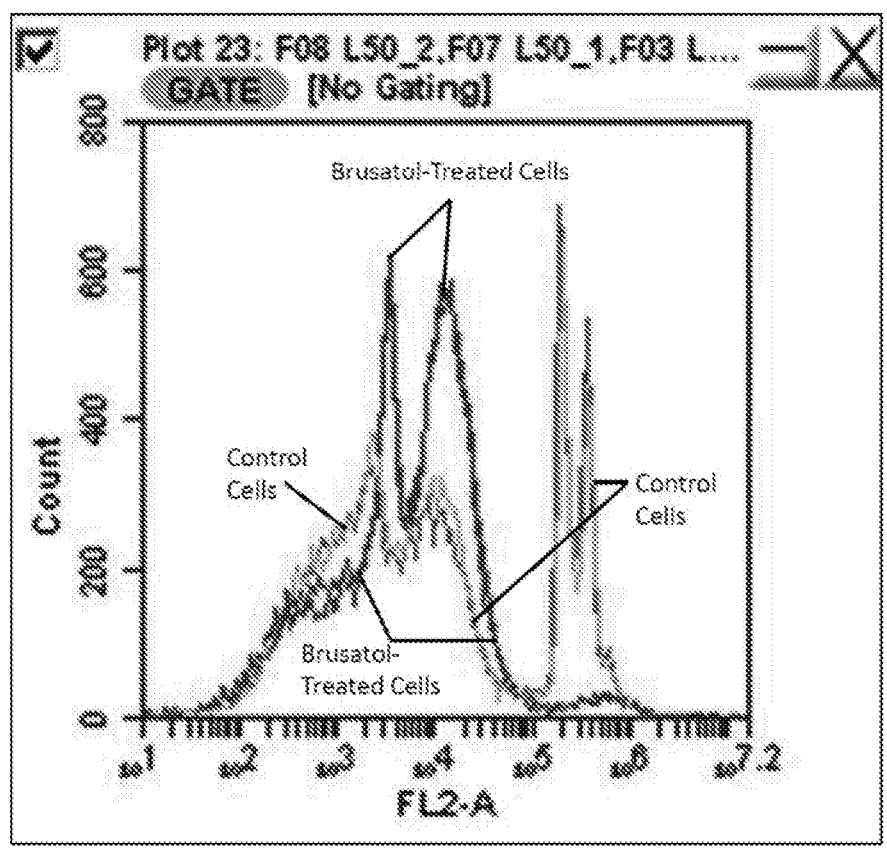
FIG. 10 is a graph showing cell cycle analysis. Treatment of LNCaP cells with brusatol (50 nM) for 120 h induces a $G_1$ arrest. Control cells (green curve); brusatol-treated cells (red curve).

Cell cycle analysis of LNCaP cells treated with 50 nM of brusatol revealed that the drug induced a $G_1$ arrest on day 5, with considerably reduced number of cells progressing to the S and $G_2$/M phases compared to control cells (FIG. 10).

Figure 11:
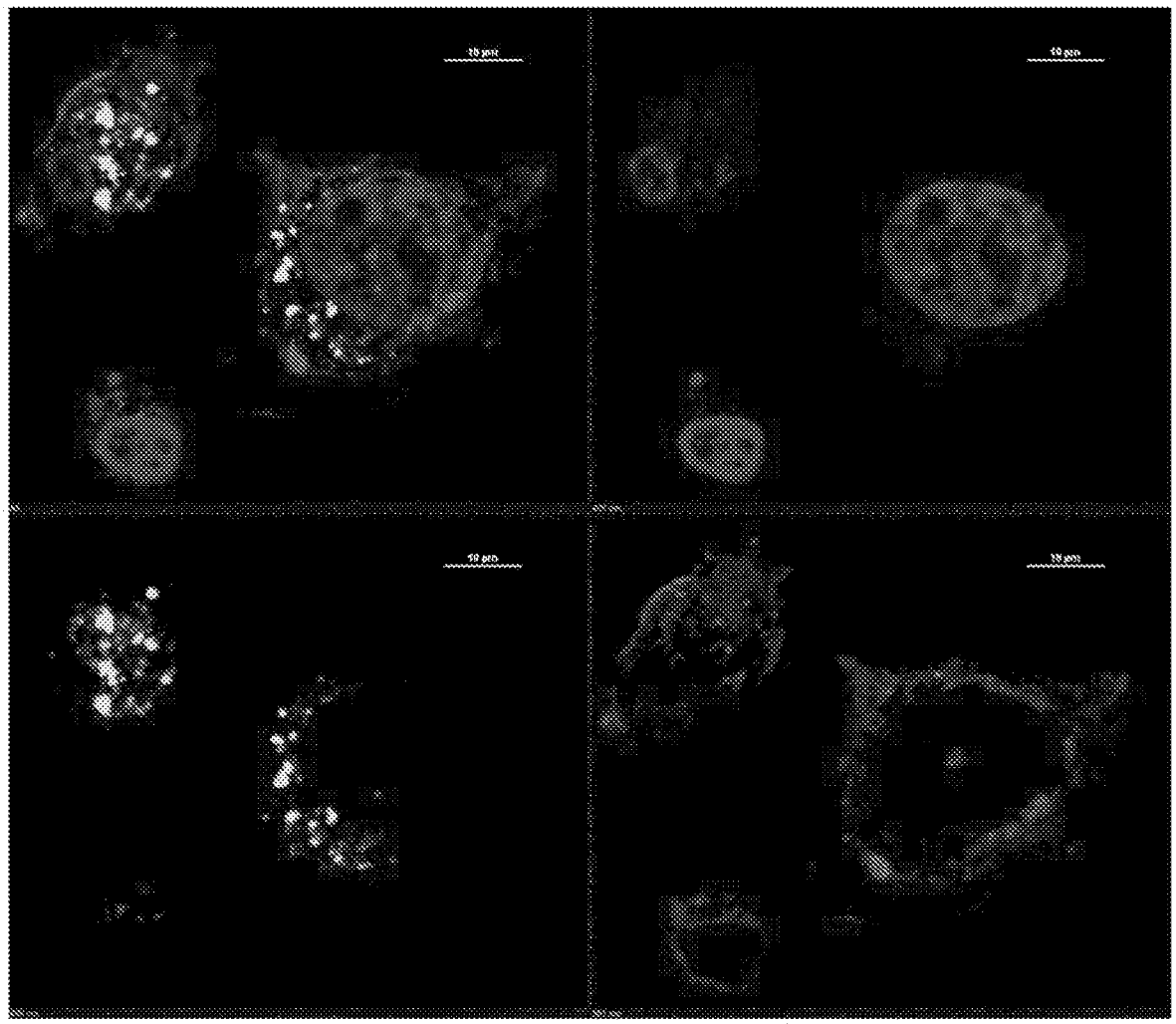
FIG. 11 shows an uptake of fluorescent nanoparticles by PC3 cells at 6 hours. Lower left quadrant shows rhodamine-123-loaded nanoparticles only; lower right quadrant shows cell membrane staining only; upper right quadrant shows nuclei staining only and upper left quadrant shows overlay of all the quadrants.
Figure 12:
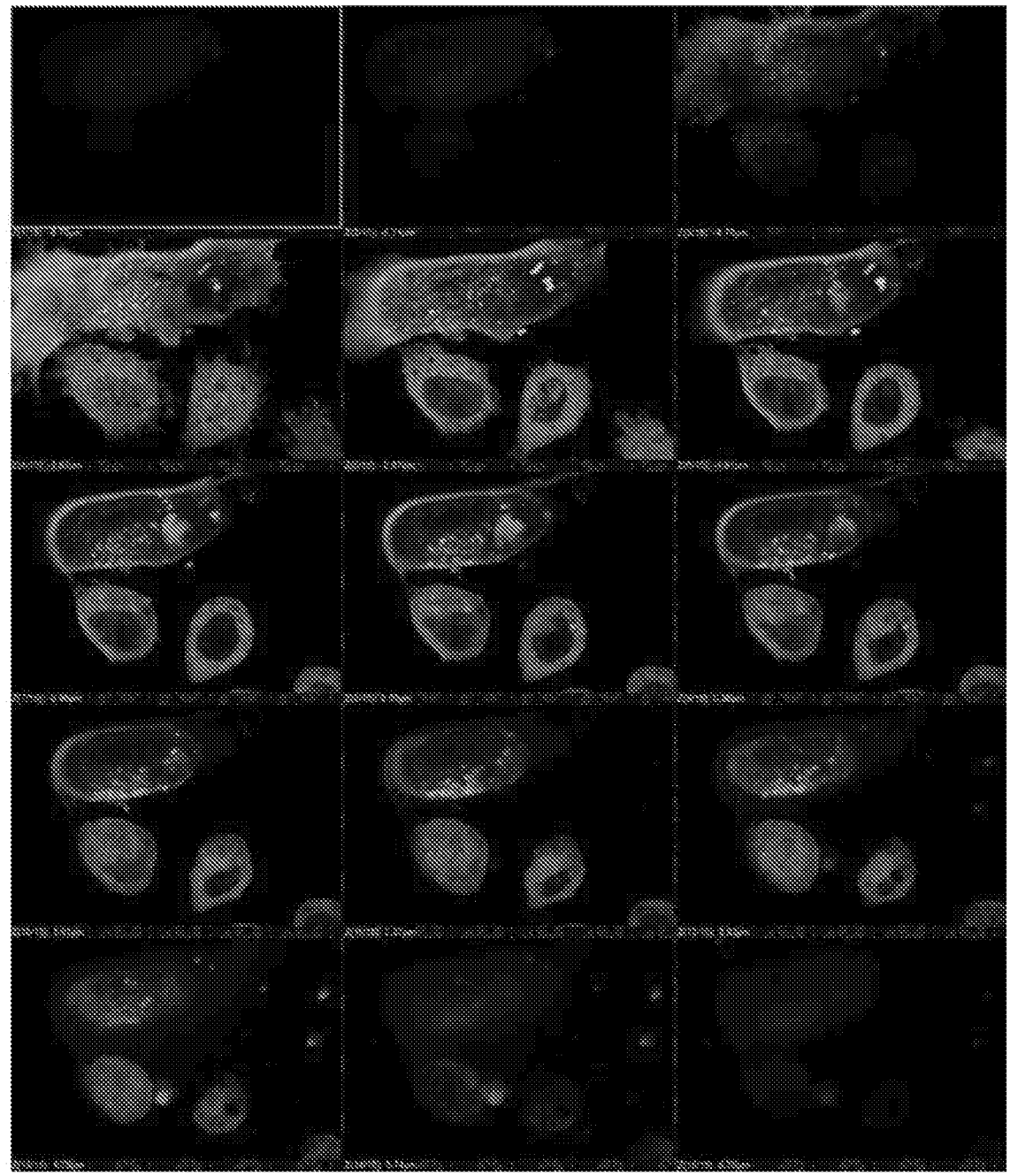
FIG. 12 shows Z-stack images confirming internalization of nanoparticles.

Cellular uptake of fluorescent nanoparticles was evaluated using confocal microscopy after a 6 hour incubation of rhodamine-123-loaded nanoparticles with PC3 cells. Our data show internalization of the nanoparticles at 6 hour. FIG. 11 shows the rhodamine-123-loaded nanoparticles (green color) around the nucleus (blue color) and enclosed by the cell membrane (red color). In addition, z-stacks images by confocal microscopy reveal the presence of nanoparticles at various depths within the cells which confirm that the nanoparticles were internalized by the cells and not adhering to the cells (FIG. 12).

PLGA-PEG was used in the fabrication of nanoparticles to facilitate prolonged circulation in blood when administered in vivo. In addition, PLGA is approved by the US Food and Drug Administration (FDA) for use in humans which makes its use for nanomedicines attractive. Kumari Avnesh, Yadav Sudesh Kumar, Yadav Subhash C., "Biodegradable polymeric nanoparticles based drug delivery systems; Colloids and Surfaces B," Biointerfaces, (2010) 75:1-18. Brusatol-loaded nanoparticles were prepared by the oil-in-water (o/w) emulsification solvent diffusion method. Scanning electron microscopy reveal the formation of smooth spherical nanoparticles (FIG. 6).

The toxicity of the brusatol-loaded nanoparticles in prostate cancer cell lines was evaluated over 120 hours using the Cell Titer 96® Non-Radioactive Cell Proliferation Assay (Promega Corp.). LNCaP cells are androgen receptor dependent while PC-3 cells are androgen independent. Majumder Pradip K., Sellers William R., "Akt-Regulated Pathways in Prostate Cancer," Oncogene, (2005) 24: 7465-7474. This allows evaluation of the effect of brusatol on both androgen dependent and androgen independent cells. The data shows that blank nanoparticles are biocompatible at the highest concentration tested which is equivalent to the amount of polymer in 500 nM of brusatol-loaded nanoparticles. Greater than 95% viability was observed in both cell lines after treatment with blank nanoparticles for 120 h. The data also confirm that the cytotoxicity observed with brusatol-loaded nanoparticles is due to the release of the encapsulated drug from the nanoparticle delivery system. In addition, the cytotoxicity observed could not be attributed to androgen sensitivity as the brusatol nanoparticle formulation was revealed to be toxic to both PC3 ($IC_{50}$ of 34.33 nM) and LNCaP ($IC_{50}$ of 16.16 nM) cell lines. This confirms its reported mechanism of action as a global inhibitor of protein synthesis and its effect on Nrf2 which are not correlated to androgen sensitivity. Furthermore, cell cycle analysis of LNCaP cells treated with brusatol solution (50 nM) revealed a $G_1$ arrest.

Statistical analysis of cytotoxicity data reveal a significant difference between the drug in solution and the nanoparticle formulation of the drug. At test concentrations close to the $IC_{50}$, the nanoparticle formulations containing brusatol were significantly more toxic to cells compared to the solution of the drug. Post hoc tests (Bonferroni) consequent to One-way Analysis of Variance (ANOVA) reveal that for PC3 cells, there was a significant difference in viability between the nanoparticle formulation and the drug in solution at the 50 nM concentration tested at 5% level of significance (p=0.000). For the LNCaP cell line, there was a significant difference in viability between the nanoparticle formulation and the drug in solution at both 10 nM (p=0.000) and 50 nM (p=0.023) concentrations at 5% level of significance. At higher concentrations, there was no significant difference in toxicity between the nanoparticle formulation and the drug solution. This may be adduced to the fact that at high concentrations, both formulations were considerably toxic to cells that any difference in toxicity between the formulations is obscured. Furthermore, statistical analysis of $IC_{50}$ data using the T test reveal that LNCaP cells are more sensitive to brusatol compared to PC3 cells at 5% level of significance (p=0.021).

In vitro drug release studies show that less than 50% of brusatol was released at 120 hours. Data from cytotoxicity studies reveal that the nanoparticle formulation was more toxic to both cancer cell lines when compared to the drug in solution formulation. Confocal microscopy studies were used to evaluate nanoparticle cellular internalization to determine the mechanism of greater cytotoxicity of the nanoparticle formulation. Data shows intense uptake of nanoparticles into the cell cytoplasm at the 6 hour time point evaluated. Thus, drug release from nanoparticles occurs in the cell cytoplasm where the nanoparticles act as intracellular drug depots by slowly releasing the encapsulated drug. This potentially leads to a sustained inhibitory effect on Nrf2 and sustained inhibition of protein synthesis in the cytoplasm thereby leading to an increase in cytotoxicity of the nanoparticle formulation.

The matter set forth in the foregoing description is offered by way of illustration only and not as a limitation. While particular embodiments have been shown and described, it will be apparent to those skilled in the art that changes and modifications may be made without departing from the broader aspects of the present application. The actual scope of the protection sought is intended to be defined in the following claims when viewed in their proper perspective based on the prior art.

What is claimed is:

1. A chemotherapeutic formulation comprising:
a nanoparticle loaded with a chemotherapeutic agent, the chemotherapeutic agent having the general Formula (1)

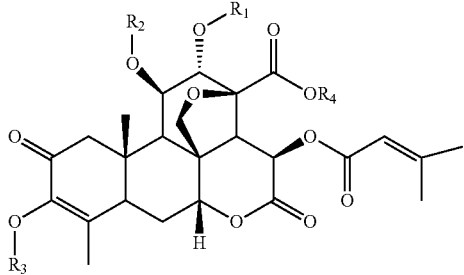

Formula (1)

wherein $R_1$, $R_2$, $R_3$ and $R_4$ are each independently selected from a site specific cleavable moiety, an alkyl, and hydrogen, and
at least one of $R_1$, $R_2$, $R_3$ and $R_4$ is a site specific cleavable moiety sensitive to a protease.

2. The chemotherapeutic formulation according to claim 1, wherein the nanoparticle is selected from the group consisting of liposomes, polymeric nanoparticles, dendrimers, inorganic nanoparticles, and polymeric micelles.

3. A chemotherapeutic formulation comprising:
a nanoparticle loaded with a chemotherapeutic agent, the chemotherapeutic agent having the general Formula (1)

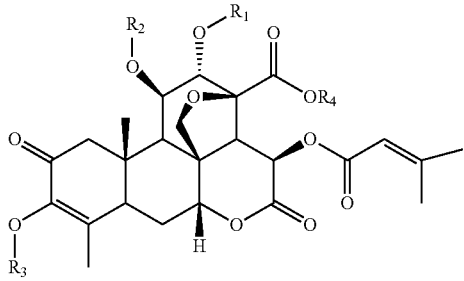

Formula (1)

wherein $R_1$, $R_2$, $R_3$ and $R_4$ are each independently selected from a site specific cleavable moiety, an alkyl, and hydrogen, and
at least one of $R_1$, $R_2$, $R_3$ and $R_4$ is a site specific cleavable moiety which comprises a peptide moiety.

4. The chemotherapeutic formulation according to claim 3, wherein at least one of $R_1$, $R_2$, $R_3$ and $R_4$ is a site specific cleavable moiety which comprises a peptide moiety comprising the sequence His-Ser-Ser-Lys-Leu-Gln-leu.

5. A chemotherapeutic formulation comprising:
a nanoparticle loaded with a chemotherapeutic agent, the chemotherapeutic agent having the general Formula (1)

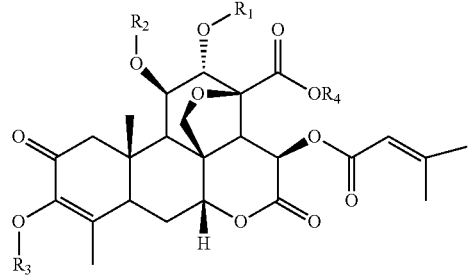

Formula (1)

wherein $R_1$, $R_2$, $R_3$ and $R_4$ are each independently selected from a site specific cleavable moiety, an alkyl, and hydrogen, and
at least one of $R_1$, $R_2$, $R_3$ and $R_4$ of the chemotherapeutic agent is a site specific cleavable moiety sensitive to glutathione.

6. The chemotherapeutic formulation according to claim 5, wherein at least one of $R_1$, $R_2$, $R_3$ and $R_4$ is a site specific cleavable moiety which comprises a disulfide bond.

7. The chemotherapeutic formulation according to claim 5, wherein at least one of $R_1$, $R_2$, $R_3$ and $R_4$ of the chemotherapeutic agent is a site specific cleavable moiety which comprises a peptide moiety containing cystine.

8. The chemotherapeutic formulation according to claim 2, wherein the nanoparticle is between 20 nm to 800 nm.

9. The chemotherapeutic formulation according to claim 2, wherein the nanoparticle comprises at least one targeting moiety selected from the group consisting of peptide moieties, carbohydrate moieties, glycoprotein moieties and aptamer moieties.

10. The chemotherapeutic formulation according to claim 9, wherein the at least one targeting moiety is a ligand for at least one of human epidermal growth factor, prostate specific membrane antigen, nucleolin, sialyl lewis X, cytotoxic T cell antigen-4, tenascin-C, platelet derived growth factor receptor, and pigpen.

11. The chemotherapeutic formulation according to claim 2, wherein the loading of the chemotherapeutic agent within the nanoparticle is between 0.2% to 50%.

12. The chemotherapeutic formulation according to claim 2, wherein the nanoparticle comprises:
   a core encapsulating the chemotherapeutic agent; and
   a corona having a hydrophilic neutral material.

13. The chemotherapeutic formulation according to claim 12, wherein the corona comprises polyethylene glycol.

14. The chemotherapeutic formulation according to claim 12, wherein the corona comprises functionalized polyethylene glycol.

15. The chemotherapeutic formulation according to claim 12, further comprising at least one targeting moiety attached to the corona.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Peptide moiety

<400> SEQUENCE: 1

His Ser Ser Lys Leu Gln Leu
1               5
```